(12) United States Patent
Tracey et al.

(10) Patent No.: US 8,822,169 B2
(45) Date of Patent: *Sep. 2, 2014

(54) HMG1 ANTIBODY FOR TREATING INFLAMMATORY CONDITIONS

(75) Inventors: Kevin J. Tracey, Old Greenwich, CT (US); Haichao Wang, Avenel, NJ (US)

(73) Assignee: The Feinstein Institute for Medical Research, Manhasset, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/402,057

(22) Filed: Feb. 22, 2012

(65) Prior Publication Data

US 2013/0028910 A1    Jan. 31, 2013

Related U.S. Application Data

(60) Continuation of application No. 12/496,333, filed on Jul. 1, 2009, now Pat. No. 8,138,141, which is a division of application No. 11/477,835, filed on Jun. 29, 2006, now Pat. No. 7,572,446, which is a continuation of application No. 10/210,747, filed on Jul. 31, 2002, now Pat. No. 7,097,838, which is a continuation of application No. 09/503,632, filed on Feb. 14, 2000, now Pat. No. 6,468,533, which is a division of application No. 09/248,574, filed on Feb. 11, 1999, now Pat. No. 6,303,321.

(51) Int. Cl.

| | |
|---|---|
| *A61P 37/00* | (2006.01) |
| *C07K 16/00* | (2006.01) |
| *A61K 39/35* | (2006.01) |
| *A61K 39/395* | (2006.01) |
| *G01N 33/68* | (2006.01) |
| *C07K 16/24* | (2006.01) |
| *A61K 39/00* | (2006.01) |

(52) U.S. Cl.
CPC ........... *A61K 39/395* (2013.01); *C07K 2316/96* (2013.01); *G01N 2800/245* (2013.01); *A61K 2039/505* (2013.01); *G01N 33/6875* (2013.01); *G01N 2800/26* (2013.01); *G01N 2800/125* (2013.01); *G01N 2800/067* (2013.01); *C07K 16/24* (2013.01); *G01N 2800/065* (2013.01)
USPC ........... 435/7.95; 514/1.4; 514/44; 424/139.1

(58) Field of Classification Search
None
See application file for complete search history.

(56) References Cited

U.S. PATENT DOCUMENTS

| | | |
|---|---|---|
| 4,678,772 A | 7/1987 | Segal et al. |
| 4,835,142 A | 5/1989 | Suzuki et al. |
| 4,871,740 A | 10/1989 | Kurono et al. |
| 5,229,378 A | 7/1993 | Ogata et al. |
| 5,425,948 A | 6/1995 | Olivieri |
| 5,530,101 A | 6/1996 | Queen et al. |
| 5,545,806 A | 8/1996 | Lonberg et al. |
| 5,545,807 A | 8/1996 | Surani et al. |
| 5,594,114 A | 1/1997 | Goodearl et al. |
| 5,605,690 A | 2/1997 | Jacobs et al. |
| 5,656,272 A | 8/1997 | Le et al. |
| 5,852,174 A | 12/1998 | Vlassara et al. |
| 5,859,205 A | 1/1999 | Adair et al. |
| 5,864,018 A | 1/1999 | Morser et al. |
| 5,885,793 A | 3/1999 | Griffiths et al. |
| 6,171,779 B1 | 1/2001 | Chada et al. |
| 6,177,077 B1 | 1/2001 | Tobinick |
| 6,303,321 B1 | 10/2001 | Tracey et al. |
| 6,323,329 B1 | 11/2001 | Bullerdiek |
| 6,329,339 B1 | 12/2001 | Pompei et al. |
| 6,448,223 B1 | 9/2002 | Tracey et al. |
| 6,468,533 B1 | 10/2002 | Tracey et al. |
| 6,468,555 B1 | 10/2002 | Nakamura |
| 6,677,321 B1 | 1/2004 | Levin |
| 6,720,472 B2 | 4/2004 | Chada et al. |
| 6,783,961 B1 | 8/2004 | Edwards et al. |
| 6,822,078 B2 | 11/2004 | Ozaki et al. |
| 7,060,504 B2 | 6/2006 | Tracey et al. |
| 7,097,838 B2 | 8/2006 | Tracey et al. |
| 7,151,082 B2 | 12/2006 | Tracey et al. |
| 7,192,917 B2 | 3/2007 | Tracey et al. |
| 7,220,723 B2 | 5/2007 | Tracey et al. |
| 7,230,078 B2 | 6/2007 | Schiffrin et al. |
| 7,288,250 B2 | 10/2007 | Newman et al. |
| 7,304,034 B2 | 12/2007 | Tracey et al. |

(Continued)

FOREIGN PATENT DOCUMENTS

| | | |
|---|---|---|
| AU | 2002247977 B2 | 3/2002 |
| EP | 0 552 439 A1 | 7/1993 |

(Continued)

OTHER PUBLICATIONS

Hertel et al., Biochime, 79:717-723, Dec. 1997.*

(Continued)

*Primary Examiner* — Daniel E Kolker
*Assistant Examiner* — Stacey N MacFarlane
(74) *Attorney, Agent, or Firm* — Hamilton, Brook, Smith & Reynolds, P.C.

(57) ABSTRACT

There is disclosed a pharmaceutical composition and method for treating sepsis, including septic shock and ARDS (acute respiratory distress syndrome), comprising administering an effective amount of a HMG1 antagonist. There is further disclosed a diagnostic method for monitoring the severity or potential lethality of sepsis or septic shock, comprising measuring the serum concentration of HMG1 in a patient exhibiting or at risk of exhibiting sepsis or septic shock symptoms. Lastly, there is disclosed a pharmaceutical composition and method for effecting weight loss or treating obesity, comprising administering an effective amount of HMG1 or a therapeutically active HMG1 fragment.

6 Claims, 10 Drawing Sheets

(56) References Cited

U.S. PATENT DOCUMENTS

| | | | |
|---|---|---|---|
| 7,537,908 | B2 | 5/2009 | Tracey et al. |
| 7,572,446 | B2 | 8/2009 | Tracey et al. |
| 7,585,504 | B2 | 9/2009 | Wu et al. |
| 7,632,500 | B2 | 12/2009 | Newman et al. |
| 7,696,169 | B2 | 4/2010 | Tracey et al. |
| 7,749,959 | B2 | 7/2010 | Tracey et al. |
| 7,897,569 | B2 | 3/2011 | Tracey et al. |
| 7,964,706 | B2 | 6/2011 | Wu et al. |
| 8,053,206 | B2 | 11/2011 | Tracey et al. |
| 8,129,130 | B2 | 3/2012 | Wu et al. |
| 8,138,141 | B2 | 3/2012 | Tracey et al. |
| 8,153,131 | B2 | 4/2012 | Wu et al. |
| 8,188,041 | B2 | 5/2012 | Tracey et al. |
| 8,501,173 | B2 | 8/2013 | Tracey et al. |
| 2002/0009749 | A1 | 1/2002 | Ozaki et al. |
| 2002/0122799 | A1 | 9/2002 | Stern et al. |
| 2002/0193432 | A1 | 12/2002 | Mjalli et al. |
| 2003/0027260 | A1 | 2/2003 | Gooddard et al. |
| 2003/0032090 | A1 | 2/2003 | Hardiman et al. |
| 2003/0032674 | A1 | 2/2003 | Hwang |
| 2003/0060410 | A1 | 3/2003 | Tracey et al. |
| 2003/0091995 | A1 | 5/2003 | Buechler et al. |
| 2003/0113323 | A1 | 6/2003 | Tracey et al. |
| 2003/0143194 | A1 | 7/2003 | Tracey et al. |
| 2003/0219741 | A1 | 11/2003 | Isogai et al. |
| 2004/0005316 | A1 | 1/2004 | Tracey et al. |
| 2004/0120953 | A1 | 6/2004 | Tracey et al. |
| 2004/0141948 | A1 | 7/2004 | O'Keefe |
| 2005/0118688 | A1 | 6/2005 | Freeze et al. |
| 2006/0030527 | A1 | 2/2006 | Mjalli et al. |
| 2006/0057679 | A1 | 3/2006 | O'Keefe et al. |
| 2006/0240019 | A1 | 10/2006 | Tracey et al. |
| 2007/0238640 | A1 | 10/2007 | Tracey et al. |
| 2008/0113385 | A1 | 5/2008 | Newman et al. |
| 2008/0167234 | A1 | 7/2008 | Tracey et al. |
| 2008/0171014 | A1 | 7/2008 | Wu et al. |
| 2008/0214454 | A1 | 9/2008 | Tracey et al. |
| 2008/0305120 | A1 | 12/2008 | Messmer et al. |
| 2009/0148453 | A1 | 6/2009 | Newman et al. |
| 2009/0263916 | A1 | 10/2009 | Tracey et al. |
| 2010/0040608 | A1 | 2/2010 | Wahren-Herlenius et al. |
| 2010/0061987 | A1 | 3/2010 | Wu et al. |
| 2010/0172905 | A1 | 7/2010 | Tracey et al. |
| 2010/0249038 | A1 | 9/2010 | Logsdon et al. |
| 2011/0020318 | A1 | 1/2011 | Tracey et al. |
| 2011/0217292 | A1 | 9/2011 | Newman et al. |
| 2011/0236406 | A1 | 9/2011 | Messmer et al. |
| 2011/0268695 | A1 | 11/2011 | Tracey et al. |
| 2011/0287023 | A1 | 11/2011 | Wu et al. |

FOREIGN PATENT DOCUMENTS

| | | |
|---|---|---|
| EP | 1 079 849 B1 | 1/2002 |
| EP | 1 165 110 B1 | 5/2006 |
| EP | 1 757 937 A2 | 2/2007 |
| EP | 1 757 937 A3 | 4/2007 |
| ES | 2137125 | 12/1999 |
| JP | 362166897 A | 1/1986 |
| JP | 10082788 | 3/1998 |
| JP | 2003 096099 | 4/2003 |
| JP | 2004 523579 | 8/2004 |
| WO | WO 96/25493 A1 | 8/1996 |
| WO | WO 97/23611 A2 | 7/1997 |
| WO | WO 98/50547 | 11/1998 |
| WO | WO 99/20756 A2 | 4/1999 |
| WO | WO 99/20756 A3 | 4/1999 |
| WO | WO 99/59609 A2 | 11/1999 |
| WO | WO 00/20621 A1 | 4/2000 |
| WO | WO 00/47104 | 8/2000 |
| WO | WO 00/55174 A | 9/2000 |
| WO | WO 00/75358 A2 | 12/2000 |
| WO | WO 01/72993 A1 | 4/2001 |
| WO | WO 01/36488 A1 | 5/2001 |
| WO | WO 01/55386 A1 | 8/2001 |
| WO | WO 01/75067 A2 | 10/2001 |
| WO | WO 01/90151 A2 | 11/2001 |
| WO | WO 01/99210 A1 | 12/2001 |
| WO | WO 02/069965 A1 | 9/2002 |
| WO | WO 02/070007 A1 | 9/2002 |
| WO | WO 02/074301 A1 | 9/2002 |
| WO | WO 02/074337 A1 | 9/2002 |
| WO | WO 02/089743 A2 | 11/2002 |
| WO | WO 02/090520 A2 | 11/2002 |
| WO | WO 02/092004 A2 | 11/2002 |
| WO | WO 03/022296 A1 | 3/2003 |
| WO | WO 03/075921 A2 | 9/2003 |
| WO | WO 2004/004763 A2 | 1/2004 |
| WO | WO 2004/044001 A2 | 5/2004 |
| WO | WO 2004/046338 A2 | 6/2004 |
| WO | WO 2004/046345 A2 | 6/2004 |
| WO | WO 2005/026209 A2 | 3/2005 |
| WO | WO 2005/034952 A2 | 4/2005 |
| WO | WO 2006/008779 A1 | 1/2006 |
| WO | WO 2006/024547 A2 | 3/2006 |
| WO | WO 2006/083301 A2 | 8/2006 |
| WO | WO 2007/001422 A2 | 1/2007 |
| WO | WO 2007/011606 A2 | 1/2007 |
| WO | WO 2007/054090 A1 | 5/2007 |
| WO | WO 2007/076200 | 7/2007 |
| WO | WO 2007/084253 A2 | 7/2007 |
| WO | WO 2008/076758 | 6/2008 |

OTHER PUBLICATIONS

Einck et al., Proc Natl Acad Sci., 80:6735-6739, Nov. 1983.*

Gombotz et al., Pharm Res., 11(5):624-632, May 1994.*

Marrugo et al., Molecular Immunology, 33(14):1119-1125, 1996.*

Abaza, M.-S. I. and Atassi, M. Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," J. Protein Chem. 11(5):433-444 (1992).

Abeyama, K., et al., "The N-terminal Domain of Thrombomodulin Sequesters High-Mobility Group—B1 Protein, a Novel Antiinflammatory Mechanism," J. Clinical Investigation 115(5):1267-1274, (May 2005).

Abraham, E., et al., "Cutting Edge: HMG-1 as a Mediator of Acute Lung Inflammation," J. Immunol., 165:2950-2954 (2000).

Aderem, A. and Ulevitch, R.J., "Toll-Like Receptors in the Induction of the Innate Immune Response," Nature, 406:782-787 (2000).

Akamatsu, H., et al., "Mechanism of Anti-Inflammatory Action of Glycyrrhizin: Effect on Neutrophil Functions Including Reactive Oxygen Species Generation," Planta Med. 57(2):119-121 (1991).

Alleva, L. M., et al., "High Mobility Group Box 1 (HMGB1) Protein: Possible Amplification Signal in the Pathogenesis of Falciparum Malaria," Trans. R. Soc. Trop. Med. Hyg., 99:171-174 (2005).

Andersson, A., et al., "Pivotal Advance: HMGB1 Expression in Active Lesions of Human and Experimental Multiple Sclerosis," J. of Leukocyte Biology, 84:1248-1255 (2008).

Andersson, U and Erlandsson-Harris, H., "HMGB1 is a Potent Trigger of Arthritis," J. Intern. Med. 255:344-350 (2004).

Andersson, U., et al., "HMGB1 as a DNA-ginding Cytokine," J. Leukocyte Biol. 72:1084-1091 (2002).

Andersson, U., et al., "High Mobility Group 1 Protein (HMG-1) Stimulates Proinflammatory Cytokine Synthesis in Human Monocytes," J. Exp. Med., 192:565-570 (2000).

Attwood, T.K., "The Babel of Bioinformatics," Science, 290:471-473 (2000).

Ayer, L. M., et al., "Antibodies to HMG Proteins in Patients With Drug-Induced Autoimmunity," Arthritis Rheum., 37(1):98-103 (1994).

Azimov, M. M., et al., "Pharmacological Study of the Anti-Inflammatory Agent Glyderinine," Farmakol. Toksikol. 51(4):90-93 (1988). English Abstract.

Banks, G. C., et al., "The HMG-I(Y) A•T-hook Peptide Motif Confers DNA-binding Specificity to a Structured Chimeric Protein," J. Biol. Chem., 274(23):16536-16544 (1999).

Baxevanis, A.D., et al., "The HMG-1 Box Protein Family: Classification and Functional Relationships," Nucleic Acids Res., 23(9):1604-1613 (1995).

(56)     References Cited

OTHER PUBLICATIONS

Benjamini, E., et al., in "*Immunology*: A Short Course," Second Ed. (NY, John Wiley & Sons, Inc.), p. 40 (1991).
Beutler, E., et al., "Synergy Between TLR2 and TLR4: A Safety Mechanism," *Blood Cells, Mol. Dis.*, 27(4):728-730 (2001).
Bianchi, E.V., et al., "Supression of ProinflammatoryCytokines in Monocytes by a Tetravalent Guanylhydrazone," *J. Exp. Med* 183:927-936 (Mar. 1996).
Bianchi, M. E., et al., "Specific Recognition of Cruciform DNA by Nuclear Protein HMG1," *Science*, 243:1056-1059 (1989).
Bianchi, M.E. and Manfredi, A.A., "High-Mobility Group Box 1 (HMGB1) Protein at the Crossroads Between Innate and Adaptive Immunity," *Immunological Reviews* 220:35-46 (2007).
Bianchi, M.E., et al., "The DNA Binding Site of HMG1 Protein is Composed of Two Similar Segments (HMG Boxes), Both of Which Have Counterparts in Other Eukaryotic Regulatory Proteins," *EMBO J.* 11(3):1055-1063 (1992).
Blank, M., et al., "Immunization With Anti-Neutrophil Cytoplasmic Antibody (ANCA) Induces the Production of Mouse ANCA and Perivascular Lymphocyte Infiltration," *Clin. Exp. Immunol.* 102:120-130 (1995).
Brennan, F.M., et al., "Role of Pro-Inflammatory Cytokines in Rheumatoid Arthritis," *Springer Semin. Immunopathol.* 20:133-147 (1998).
Bustin M., "Regulation of DNA-Dependent Activities by the functional Motifs of the High-Mobility-Group Chromosomal Proteins," *Mol. Cell. Biol.* 19(8):5237-46 (1999).
Bustin, M. "Revised Nomenclature for High Mobility Group (HMG) Chromosomal Proteins," *Trends Biochem. Sci.*, 26:152-153 (2001).
Bustin, M., et al., "Antigenic Determinants of High Mobility Group Chromosomal Proteins 1 and 2," *Biochem.*, 21:6773-6777 (1982).
Bustin, M., et al., "Immunological Relatedness of High Mobility Group Chromosomal Proteins from Calf Thymus," *J. Biol. Chem.*, 253(5):1694-1699 (1978).
Cābart, P., et al., "Differential Expression of Nuclear HMG1, HMG2 Proteins and H1⁰ Histone in Various Blood Cells," *Cell Biochemistry and Function* 13:125-133 (1995).
Chou, D. K. H., et al., "Identity of Nuclear High-Mobility-Group Protein, HMG-1, and Sulfoglucuronyl Carbohydrate-Binding Protein, SBP-1, in Brain," *J. Neurochem.*, 77:120-131 (2001).
Clackson, T., et al., "Making Antibody Fragments Using Phage Display Libraries," *Nature*, 352:624-628 (1991).
Colman, P. M., "Effects of Amino Acid Sequence Changes on Antibody-Antigen Interactions," *Res. Immunol.*, 145(1):33-36 (1994).
Czura, C., et al., "Dual Roles for HMGB1: DNA Binding and Cytokine," *J. Endotoxin Res.*, 7(4):315-321 (2001).
Czura, C., et al., "High Mobility Group Box-1 as a Therapeutic Target downstream of Tumor Necrosis Factor," *JID* 187 (Suppl 2):S391-S396 (2003).
Czura, C.J., et al., "HMGB1 in the Immunology of Sepsis (not septic shock) and Arthritis," *Advances in Immunology* 84:181-200 (2004).
Dallman, M.J., "Cytokines and transplantation: Th1/Th2 regulation of the immune response to solid organ transplants in the adult,"*Curr Opin Immunol*, 7:632-638 (1995).
Daston, M. M. and Ratner, N., "Expression of P30, a Protein with Adhesive Properties, in Schwann Cells and Neurons of the Developing and Regenerating Peripheral Nerve," *J. Cell Biol.*, 112(6):1229-1239 (1991).
Davidson, N.J., "The Therapeutic Potential of Anti-Cytokine Antibodies in the Treatment of Chronic Inflammatory Disease," *Exp. Opin. Invest. Drugs* 7(7):1115-1120 (1998).
Degryse, B., et al., "The High Mobility Group (HMG) Boxes of the Nuclear Protein HMG1 Induce Chemotaxis and Cytoskeleton Reorganization in Rat Smooth Muscle Cells," *J. Cell Biol.*, 152:1197-1206 (2001).
Di Carlo, E., et al., "Interaction Between Endothelial Cells and the Secreted Cytokine Drives the Fate of an IL4- or an IL5-Transduced Tumour," *J. Pathol.* 186:390-397 (1998).
Dorland's Illustrated Medical Dictionary, 28th ed. (Philadelphia, W.B. Saunders Co.), 1994, p. 269.

Dunn, M.D., Ph.D., D.L., "Role of Endotoxin and Host Cytokines in Spetic Shock," *Chest* 100(3):164S-168S (Sep. 1991 Supplement).
Ekström, P.A.R., et al., "The Immune Modulator Linomide Prevents Neuronal Death in Injured Peripheral Nerves of the Mouse," *NeuroReport* 9(7):1337-1341 (1998).
Elkarim, R.A., et al., "Recovery From Guillain-Barré Syndrome is Associated With Increased Levels of Neutralizing Autoantibodies to Interferon-γ," *Clinical Immunology and Immunopathology* 88(3):241-248 (1998).
Falciola, L., et al., "High Mobility Group 1 Protein is Not Stably Associated with the Chromosomes of Somatic Cells," *J. Cell Biol.*, 137 (1):19-26 (1997).
Fallon, M.T. and Hanks, G.W., "Control of Common Symptoms in Advanced Cancer," *Ann. Acad. Med. Singapore* 23(2):171-177 (1994).
Fei, J., et al., "Study on High Mobility Group-1 Protein in Patients with Multiple Trauma," *Zhongguo Wei Zhong Bing Ji Jiu Yi Xue*, 17(5):273-275 (2005).
Fiuza, C., et al. "Inflammation-Promoting Activity of HMGB1 on Human Microvascular Endothelial Cells," *Blood* 101(7): 2652-2660 (2003).
Freeman, B. D., et al., "The Role of Inflammation in Sepsis and Septic Shock: A Meta-Analysis of Both Clinical and Preclinical Trials of Anti-Inflammatory Therapies," in *Inflammation: Basic Principals and Clinical Correlates* (John I. Gallin and Ralph Snyderman eds., Lippincott, Williams & Wilkins, Philadelphia, 3$^{rd}$ ed. 1999), pp. 965-975.
GenBank Accession No. AAA20508, "HMG-1," (1994) [online] [retrieved on Mar. 21, 2006]. Retrieved from the Internet: <URL:http://www.ncbi.nlm.nih.gov/entrez/viewer.fcgi?db=protein&val=437102>.
GenBank Accession No. AAA64970, "HMG-1," (1995) [online] [retrieved on Sep. 30, 2004]. Retrieved from the Internet: <URL:http://www.ncbi.nlm.nih.gov/entrez/viewer.fcgi?db=protein&val=184251>.
GenBank Accession No. AAB08987, "Non-Histone Chromatin Protein HMG1 [*Homo sapiens*]," (1996) [online] [retrieved on Mar. 21, 2006]. Retrieved from the Internet: <URL:http://www.ncbi.nlm.nih.gov/entrez/viewer.fcgi?db=protein&val=1435197>.
GenBank Accession No. AB009451, "Alternaria alternata MAT1 Gene, Complete cds," (2002) [online] [retrieved on Mar. 21, 2006]. Retrieved from the Internet: <URL:http://www.ncbi.nlm.nih.gov/entrez/viewer.fcgi?db=nuccore&val=4520345>.
GenBank Accession No. AC010149, "*Homo sapiens*BAC clone RP11-395A23 from 2, complete sequence," (2005) [online] [retrieved on Apr. 18, 2006]. Retrieved from the Internet: <URL:http://www.ncbi.nlm.nih.gov/entrez/viewer.fcgi?db=nuccore&val=14151041>.
GenBank Accession No. AF076674, "*Homo sapiens*high mobility group 1-like protein L1 (HMG1L1) retropseudogene sequence," (1999) [online] [retrieved on Apr. 18, 2006]. Retrieved from the Internet: <URL:http://www.ncbi.nlm.nih.gov/entrez/viewer.fcgi?db=nuccore&val=4884556>.
GenBank Accession No. AF076676, "*Homo sapiens*high mobility group 1-like protein L4 (HMG1L4) retropseudogene sequence," (1999) [online] [retrieved on Apr. 18, 2006]. Retrieved from the Internet: <URL:http://www.ncbi.nlm.nih.gov/entrez/viewer.fcgi?db=nuccore&val=4884558>.
GenBank Accession No. AF107043, "*Homo sapiens*Clone pCL11 DNA-binding Protein SOX14 (SOX14) Gene, Complete cds," (1998) [online] [retrieved on Mar. 21, 2006]. Retrieved from the Internet: <URL:http://www.ncbi.nlm.nih.gov/entrez/viewer.fcgi?db=nuccore&val=4008100>.
GenBank Accession No. AF107044, "*Homo sapiens*Clone pCL4 DNA-binding Protein SOX21 (SOX21) Gene, Complete cds," (1998) [online] [retrieved on Mar. 21, 2006]. Retrieved from the Internet: <URL:http://www.ncbi.nlm.nih.gov/entrez/viewer.fcgi?db=nuccore&val=4008102>.
GenBank Accession No. AF165167, "*Homo sapiens*high mobility group 1-like protein L8 (HMG1L8) retropseudogene, complete sequence," (2001) [online] [retrieved on Apr. 21, 2006]. Retrieved from the Internet: <URL:http://www.ncbi.nlm.nih.gov>.

(56) References Cited

OTHER PUBLICATIONS

GenBank Accession No. AF165168, "*Homo sapiens*high mobility group 1-like protein L9 (HMG1L9) retropseudogene, complete sequence," (2001) [online] [retrieved on Apr. 18, 2006]. Retrieved from the Internet: <URL:http://www.ncbi.nlm.nih.gov>.
GenBank Accession No. AF226675, "*Homo sapiens*Transcription Factor SOX8 mRNA, Complete cds," (2000) [online] [retrieved on Mar. 21, 2006]. Retrieved from the Internet: <URL:http://www.ncbi.nlm.nih.gov/entrez/viewer.fcgi?db=nuccore&val=7025446>.
GenBank Accession No. AF309034, "*Homo sapiens*SOX6 mRNA, Complete cds," (2001) [online] [retrieved on Mar. 21, 2006]. Retrieved from the Internet: <URL:http://www.ncbi.nlm.nih.gov/entrez/viewer.fcgi?db=nuccore&val=13435017>.
GenBank Accession No. AJ001183, "*Homo sapiens*mRNA for Sox10 Protein," (2005) [online] [retrieved on Mar. 21, 2006]. Retrieved from the Internet: <URL:http://www.ncbi.nlm.nih.gov/entrez/viewer.fcgi?db=nuccore&val=2909359>.
GenBank Accession No. CAA31110, "Unnamed Protein Product [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=32327>.
GenBank Accession No. D30765, "*Xenopus laevis* mRNA for HMG-X Protein, Complete cds," (1999) [online] [retrieved on Mar. 21, 2006]. Retrieved from the Internet: <URL:http://www.ncbi.nlm.nih.gov/entrez/viewer.fcgi?db=nuccore&val=639690>.
GenBank Accession No. J04197, "*Rattus norvegicus* 6-phosphofructo-2-kinase/fructose-2, 6-bisphosphatase mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=202557>.
GenBank Accession No. L17131, "*Homo sapiens*High Mobility Group Protein (HMG-I(Y)) Gene Exons 1-8, Complete cds" (1999) [online] [retrieved on Mar. 21, 2006]. Retrieved from the Internet: <URL:http://www.ncbi.nlm.nih.gov/entrez/viewer.fcgi?db=nuccore&val=306868>.
GenBank Accession No. L32859, "Rainbow Trout HMG-I Gene Exons 2-5, Complete cds," (1995) [online] [retrieved on Mar. 21, 2006]. Retrieved from the Internet: <URL:http://www.ncbi.nlm.nih.gov/entrez/viewer.fcgi?db=nuccore&val=609550>.
GenBank Accession No. M23618, "Human HMG-Y Protein Isoform mRNA (HMGI gene), Clone 11D," (1996) [online] [retrieved on Mar. 21, 2006]. Retrieved from the Internet: <URL:http://www.ncbi.nlm.nih.gov/entrez/viewer.fcgi?db=nuccore&val=184258>.
GenBank Accession No. M62810, "Human Mitochondrial Transcription Factor 1 mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=188563>.
GenBank Accession No. M74017, "*T. brucei* Rhodesiense HMG1-like Protein mRNA, Complete cds" (1993) [online] [retrieved on Mar. 21, 2006]. Retrieved from the Internet: <URL:http://www.ncbi.nlm.nih.gov/entrez/viewer.fcgi?db=nuccore&val=162108>.
GenBank Accession No. M83665, "Human High Mobility Group 2 Protein (HMG-2) gene, Complete cds," (1994) [online] [retrieved on Sep. 24, 2004]. Retrieved from the Internet: <URL:http://www.ncbi.nlm.nih.gov/entrez/viewer.fcgi?db=nuccore&val=184235>.
GenBank Accession No. M86737, "Human High Mobility Group Box (SSRP1) mRNA, Complete cds," (1994) [online] [retrieved on Mar. 21, 2006]. Retrieved from the Internet: <URL:http://www.ncbi.nlm.nih.gov/entrez/viewer.fcgi?db=nuccore&val=184241>.
GenBank Accession No. NG_000897, "*Homo sapiens*high-mobility group (nonhistone chromosomal) protein 1-like 5 (HMG1L5) pseudogene on chromosome 3," (2002) [online] [retrieved on Apr. 18, 2006]. Retrieved from the Internet: <URL:http://www.ncbi.nlm.nih.gov>.
GenBank Accession No. NM_005342, "*Homo sapiens*High-mobility Group Box 3 (HMGB3), mRNA," (2005) [online] [retrieved on Mar. 21, 2006]. Retrieved from the Internet: <URL:http://www.ncbi.nlm.nih.gov/entrez/viewer.fcgi?db=nuccore &val=71143136>.
GenBank Accession No. NM_016957, "*Mus musculus* High Mobility Group Nucleosomal Binding Domain 2 (Hmgn2), mRNA," (2006) [online] [retrieved on Mar. 21, 2006]. Retrieved from the Internet: <URL:http://www.ncbi.nlm.nih.gov/entrez/viewer.fcgi?db=nuccore&val=86198321>.
GenBank Accession No. NP_002119, "High-Mobility Group Box 1 [*Homo sapiens*]," (2006) [online] [retrieved on Mar. 21, 2006]. Retrieved from the Internet: <URL:http://www.ncbi.nlm.nih.gov/entrez/viewer.fcgi?db=protein&val=4504425>.
GenBank Accession No. NP_005333, "High-Mobility Group Box 3 [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=71143137>.
GenBank Accession No. O00479, "Nonhistone Chromosomal Protein HMG-17-like 3 (Non-Histone Chromosomal Protein) (High-Mobility Group Nucleosome Binding Domain 4)," (2005) [online] [retrieved on Mar. 21, 2006]. Retrieved from the Internet: <URL:http://www.ncbi.nlm.nih.gov/entrez/viewer.fcgi?db=protein&val=20138140>.
GenBank Accession No. P05114, "Nonhistone Chromosomal Protein HMG-14 (High-Mobility Group Nucleosome-Binding Domain 1)," (1987) [online] [retrieved on Mar. 24, 2006]. Retrieved from the Internet: <URL:http://www.ncbi.nlm.nih.gov/entrez/viewer.fcgi?db=protein&val=123101>.
GenBank Accession No. P07155, "High Mobility Group Protein 1 (HMG-1) (Amphoterin) (Heparin-Binding Protein p30)," (2004) [online] [retrieved on Mar. 21, 2006]. Retrieved from the Internet: <URL:http://www.ncbi.nlm.nih.gov/entrez/viewer.fcgi?db=protein&val=1708258>.
GenBank Accession No. P09429, "High Mobility Group Protein 1 (HMG-1) (High Mobility Group Protein B1," (1989) [online] [retrieved on Mar. 21, 2006]. Retrieved from the Internet: <URL:http://www.ncbi.nlm.nih.gov/entrez/viewer.fcgi?db=protein&val=123369>.
GenBank Accession No. S02826, "Nonhistone Chromosomal Protein HMG-1—human," (1999) [online] [retrieved on Apr. 18, 2006]. Retrieved from the Internet: <URL:http://www.ncbi.nlm.nih.gov/entrez/viewer.fcgi?db=protein&val=88270>.
GenBank Accession No. S29857, "Nonhistone Chromosomal Protein HMG-1—Human," (1999) [online] [retrieved on Mar. 21, 2006]. Retrieved from the Internet: <URL:http://www.ncbi.nlm.nih.gov/entrez/viewer.fcgi?db=protein&val=478813>.
GenBank Accession No. U00431, "*Mus musculus* HMG-1 mRNA, Complete cds" (1994) [online] [retrieved on Mar. 21, 2006]. Retrieved from the Internet: <URL:http://www.ncbi.nlm.nih.gov/entrez/viewer.fcgi?db=nuccore&val=437101>.
GenBank Accession No. U13695, "Human Homolog of Yeast mutL (hPMS1) Gene, Complete cds," (1995) [online] [retrieved on Mar. 21, 2006]. Retrieved from the Internet: <URL:http://www.ncbi.nlm.nih.gov/entrez/viewer.fcgi?db=nuccore&val=535512>.
GenBank Accession No. U36501, "Human SP100-B (SP100-B) mRNA, Complete cds," (1996) [online] [retrieved on Mar. 21, 2006]. Retrieved from the Internet: <URL:http://www.ncbi.nlm.nih.gov/entrez/viewer.fcgi?db=nuccore&val=1173655>.
GenBank Accession No. U51677, "Human non-histone chromatin protein HMG1 (HMG1) gene, complete cds.," (1996) [online] [retrieved on Mar. 21, 2006]. Retrieved from the Internet: <URL:http://www.ncbi.nlm.nih.gov/entrez/viewer.fcgi?db=nuccore&val=1435196>.
GenBank Accession No. X02666, "Trout mRNA for High Mobility Group Protein HMG-T," (2005) [online] [retrieved on Mar. 21, 2006]. Retrieved from the Internet: <URL:http://www.ncbi.nlm.nih.gov/entrez/viewer.fcgi?db=nuccore&val=64327>.
GenBank Accession No. X13546, "Human HMG-17 Gene for Nonhistone Chromosomal Protein HMG-17," (1997) [online] [retrieved on Mar. 21, 2006]. Retrieved from the Internet: <URL:http://www.ncbi.nlm.nih.gov/entrez/viewer.fcgi?db=nuccore&val=32328>.
GenBank Accession No. X53390, "Human mRNA for Upstream Binding Factor (hUBF)," (1999) [online] [retrieved on Mar. 21, 2006]. Retrieved from the Internet: <URL:http://www.ncbi.nlm.nih.gov/entrez/viewer.fcgi?db=nuccore&val=509240>.
GenBank Accession No. X53431, "Yeast Gene for STE11," (2005) [online] [retrieved on Mar. 21, 2006]. Retrieved from the Internet: <URL:http://www.ncbi.nlm.nih.gov/entrez/viewer.fcgi?db=nuccore&val=4553>.

(56) References Cited

OTHER PUBLICATIONS

GenBank Accession No. X53772, "*H. sapiens* SRY Gene," (1997) [online] [retrieved on Mar. 21, 2006]. Retrieved from the Internet: <URL:http://www.ncbi.nlm.nih.gov/entrez/viewer.fcgi?db=nuccore&val=36604>.

GenBank Accession No. X58636, "Mouse LEF1 mRNA for Lymphoid Enhancer Binding Factor 1," (1999) [online] [retrieved on Mar. 21, 2006]. Retrieved from the Internet: <URL:http://www.ncbi.nlm.nih.gov/entrez/viewer.fcgi?db=nuccore&val=52887>.

GenBank Accession No. X59869, "Human TCF-1 mRNA for T Cell Factor 1 (Splice Form A)," (2005) [online] [retrieved on Mar. 21, 2006]. Retrieved from the Internet: <URL:http://www.ncbi.nlm.nih.gov/entrez/viewer.fcgi?db=nuccore&val=36785>.

GenBank Accession No. X67668, "*M. musculus* mRNA for high mobility group 2 protein," (2005) [online] [retrieved on Apr. 18, 2006]. Retrieved from the Internet: <URL:http://www.ncbi.nlm.nih.gov/entrez/viewer.fcgi?db=nuccore&val=51338>.

GenBank Accession No. X71135, "*H. sapiens* Sox3 Gene," (2005) [online] [retrieved on Mar. 21, 2006]. Retrieved from the Internet: <URL:http://www.ncbi.nlm.nih.gov/entrez/viewer.fcgi?db=nuccore&val=468790>.

GenBank Accession No. X71138, "*D. melanogaster* HMG-D mRNA," (1993) [online] [retrieved on Mar. 21, 2006]. Retrieved from the Internet: <URL:http://www.ncbi.nlm.nih.gov/entrez/viewer.fcgi?db=nuccore&val=296942>.

GenBank Accession No. X71139, "*D. melanogaster* HMG-Z mRNA," (2005) [online] [retrieved on Mar. 21, 2006]. Retrieved from the Internet: <URL:http://www.ncbi.nlm.nih.gov/entrez/viewer.fcgi?db=nuccore&val=296944>.

GenBank Accession No. X73039, "*H. sapiens* SOX-12 Gene," (2005) [online] [retrieved on Mar. 21, 2006]. Retrieved from the Internet: <URL:http://www.ncbi.nlm.nih.gov/entrez/viewer.fcgi?db=nuccore&val=312151>.

GenBank Accession No. XM_063129, "*Homo sapiens*similar to high mobility group 1 (LOC122441), mRNA," (2002) [online] [retrieved on Apr. 18, 2006]. Retrieved from the Internet: <URL:http://www.ncbi.nlm.nih.gov/entrez/viewer.fcgi?db=nuccore&val=17453404>.

GenBank Accession No. XM_066789, "*Homo sapiens*similar to high mobility group 1 (LOC139603), mRNA," (2002) [online] [retrieved on Apr. 18, 2006]. Retrieved from the Internet: <URL:http://www.ncbi.nlm.nih.gov>.

GenBank Accession No. Y13436, "*Homo sapiens*Sox 1 Gene," (2005) [online] [retrieved on Mar. 21, 2006]. Retrieved from the Internet: <URL:http://www.ncbi.nlm.nih.gov/entrez/viewer.fcgi?db=nuccore&val=4128158>.

GenBank Accession No. Z11540, "*T. aestivum* mRNA for High Mobility Group Protein (HMGW)," (2005) [online] [retrieved on Mar. 21, 2006]. Retrieved from the Internet: <URL:http://www.ncbi.nlm.nih.gov/entrez/viewer.fcgi?db=nuccore&val=21802>.

GenBank Accession No. Z31560, "*H. sapiens* Sox-2 mRNA (partial)," (2005) [online] [retrieved on Mar. 21, 2006]. Retrieved from the Internet: <URL:http://www.ncbi.nlm.nih.gov/entrez/viewer.fcgi?db=nuccore&val=854181>.

GenBank Accession No. Z48008, "*S. cerevisiae* Chromosome IV Cosmid 8119," (2005) [online] [retrieved on Mar. 21, 2006]. Retrieved from the Internet: <URL:http://www.ncbi.nlm.nih.gov/entrez/viewer.fcgi?db=nuccore&val=642799>.

Goldstein, R.S., et al. "HMGB1 Detection in Patients with Cerebral and Myocardial Ischemia," J. Invest. Med., 53(2): 5387 (2005) (Abstract From Joint Annual Meeting of the Central-Society-for-Clinical-Research/Midwestern American-Federation-for-Medical-Research).

Gonzalez, E.R., and Kannewurf. B.S., "Atherosclerosis: A Unifying Disorder With Diverse Manifestations," *Am. J. Health-Syst. Pharm.* 55(Suppl 1):S4-S7 (1998).

Harrison's Principles of Internal Medicine, 17th ed., pp. 1680-1684 (2008).

Heeringa, P., et al., "Autoantibodies to Myeloperoxidase Aggravate Mild Anti-Glomerular-Basement-Membrane-Mediated Glomerular Injury in the Rat," *Am. J. Pathol.* 149(5):1695-1706 (1996).

Hermann, J., et al., "Cytokine Therapy in Rheumatoid Arthritis," *Springer Semin Immunopathol* 20:275-288 (1998).

"High Mobility Group, (HMG) Chromosomal Proteins Nomenclature Home Page" [online] [retrieved on Nov. 7, 2005], retrieved from the Internet :< URL:http://www.informatics.jax.org/mgihome/nomen/genefamilies/hmgfamily.shtml>.

Hori, O., et al., "The Receptor for Advanced Glycation End Products (RAGE) Is a Cellular Binding Site for Amphoterin," *J. Biol. Chem.*, 270(43):25752-25761 (1995).

Hou, CC., et al., "Expression of High Mobility Group Box-1 in the Lung Tissue of BALF of Asthmatic Mice and the Influence of Dexamethasone," Nan Fang Yi Ke Da Xue Xue Bao 30(9):2051-2054 (2010). (Abstract only).

Huttunen, H.J., "Receptor for Advanced Glycation End Products-Binding COOH-Terminal Motif of Amphoterin Inhibits Invasive Migration and Metastasis," Cancer Res., 62(16)4805-4811 (2002).

Imamura, T., et al., "Interaction with p53 Enhances Binding of Cisplatin-Modified DNA by High Mobility Group 1 Protein," *J. Biol. Chem.*, 276(10):7534-7540 (2001).

Ise, T., et al., "Transcription Factor Y-Box Binding Protein 1 Binds Preferentially to Cisplatin-Modified DNA and Interacts With Proliferating Cell Nuclear Antigen," *Cancer Res.*, 59:342-346 (1999).

Iwaki, D., et al., "The Extracellular Toll-Like Receptor 2 Domain Directly Binds Peptidoglycan Derived from *Staphylococcus aureus*," *J. Biol. Chem.*, 277(27):24315-24320 (2002).

Jakobovits, A., et al., "Analysis of Homozygous Mutant Chimeric Mice: Deletion of the Immunoglobulin Heavy-Chain Joining Region Blocks B-Cell Development and Antibody Production," *Proc. Natl. Acad. Sci. USA*, 90:2551-2555 (1993).

Jakobovits, A., et al., "Germ-Line Transmission and Expression of a Human-Derived Yeast Artificial Chromosome," *Nature*, 362:255-258 (1993).

James, J.S. and Dubs, G., "FDA Approves New Kind of Lymphoma Treatment," *AIDS Treatment News* pp. 1-3, (Dec. 1997).

Janeway, Jr., C.A., et al. Immuno Biology The Immune System in Health and Disease, 3rd Ed. Garland Publishing Inc. pp. 2:9 and 2:23 (1997).

Janeway, Jr., C.A., "Approaching the Asymptote? Evolution and Revolution in Immunology," Cold Spring Harbor Syposia on Quantitative Biology Voil. LIV, downloaded from symposium.cship.org Apr. 7, 2011. pp. 1-13.

Jayne, D.R.W., et al., "ANCA Anti-Idiotype Antibodies and the Treatment of Systemic Vasculitis With Intravenous Immunoglobulin," *J. Autoimmunity* 6:207-219 (1993).

Johns, E.W., et al. "History, Definitions and Problems," in *The HMG Chromsomal Problems*, (Academic Press), London: Chapter 1, pp. 1-7 (1982).

Jones, B. W., et al., "Different Toll-Like Receptor Agonists Induce Distinct Macrophage Responses," *J. Leukoc. Biol.*, 69(6):1036-1044 (2001).

Jorens, P.G., et al., "High Levels of Leukaemia Inhibitory Factor in ARDS," *Cytokine* 8(11):873-876 (1996).

Jouvenne, P., et al., "Increased Incidence of Neutralizing Autoantibodies Against Interleukin-1α (IL-1α) in Nondestructive Chronic Polyarthritis," *J. Clin. Immunol.* 16(5):283-290 (1996).

Jung, F., et al., "Antibodies Against a Peptide Sequence Located in the Linker Region of the HMG-1/2 Box Domains in Sera From Patients With Juvenile Rheumatoid Arthritis," *Arthritis Rheum.*, 40(10):1803-1809 (1997).

Kabir, S., et al., "Serum Levels of Interleukin-1, Interleukin-6 and Tumour Necrosis Factor-Alpha in Patients With Gastric Carcinoma," *Cancer Letters* 95:207-212 (1995).

Kakumu, S., et al., "Serum Levels of IL-10, IL-15 and Soluble Tumour Necrosis Factor-alpha (TNF-α) Receptors in Type C Chronic Liver Disease," *Clin. Exp. Immunol.*, 109:458-463 (1997).

Kalinina, N., et al., "Increased Expression of the DNA-Binding Cytokine HMGB1 in Human Atherosclerotic Lesions: Role of Activated Macrophages and Cytokines," *Arterioscler. Thromb. Vasc. Biol.*, 24: 2320-2325 (2004).

(56) References Cited

OTHER PUBLICATIONS

Kawahara, N., et al., "Enhanced Coexpression of Thioredoxin and High Mobility Group Protein 1 Genes in Human Hepatocellular Carcinoma and the Possible Association With Decreased Sensitivity to Cisplatin," *Cancer Research* 56:5330-5333 (1996).

Kim, J., et al., "Activation of Toll-Like Receptor 2 in Acne Triggers Inflammatory Cytokine Responses," *J. Immunol.*, 169(3):1535-1541 (2002).

Kirschning, C.J., et al., "Human Toll-Like Receptor 2 Confers Responsiveness to Bacterial Lipopolysaccharide," *J. Exp. Med.*, 188(11):2091-2097 (1998).

Klimczak, L.J., et al. "Microheterogeneous Cytosolic High-Mobility Group Proteins from Broccoli Co-Purify with and Are Phosphorylated by Casein Kinase II," *Plant Physiology*, 105:911-919 (1994).

Kobayashi, K., et al., "Aggravation of Rat Nephrotoxic Serum Nephritis by Anti-Myeloperoxidase Antibodies," *Kidney International* 47:454-463 (1995).

Kokkola, R., et al., "High Mobility Group Box Chromosomal Protein 1," *Arthritis Rheum.*, 46(10):2598-2603 (2002).

Kokkola, R., et al., "Successful Treatment of Collagen-Induced Arthritis in Mice and Rats by Targeting Extracellular High Mobility Group Box Chromosomal Protein 1 Activity," *Arthritis & Rheumatism* 48(7):2052-2058 (Jul. 2003).

Krenger, W. and Ferrara, J.L.M., "Graft-versus-Host Disease and the Th1/Th2 Paradigm," *Immunol Res*, 15:50-73 (1996).

Kuby, J., *Immunology*, (New York, W.H. Freeman and Company) 1992, p. 1-20.

Kuntz, I.D., "Structure-Based Strategies for Drug Design and Discovery," *Science*, 257:1078-1082 (1992).

Landsman, D., et al., "A Signature for the HMG-1 Box DNA-Binding Proteins," *BioEssays*, 15(8):539-546 (1993).

Lederman, S., et al., "A Single Amino Acid Substitution in a Common African Allele of the CD4 Molecule Ablates Binding of the Monoclonal Antibody OKT," *Mol. Immunol.*, 28(11):1171-1181 (1991).

Levy, M.M., et al., 2001 SCCM/ESICM/ACCP/ATS/SIS International Sepsis Definitions Conference, *Intensive Care Med* 29:530-538 (2003).

Li, C.H., et al., "beta-Endorphin Omission Analogs: Dissociation of Immunoreactivity from Other Biological Activities," *Proc. Natl. Acad. Sci.*, 77:3211-3214 (1980).

Li, J., et al. "Structural Basis for the Proinflammatory Cytokine Activity of High Mobility Group Box 1," *Molecular Medicine* 9:37-45 (2003).

Li, M., et al., "An Essential Role of the NF-κB/Toll Like Receptor Pathway in Induction of Inflammatory and Tissue Repair Gene Expression by Necrotic Cells," *J. Immunol.*, 166:7128-7135 (2001).

Li, M., et al., "Recombinant HMGB1 with cytokine-stimulating activity," *J. Immunol. Methods*, 289:211-223 (2004).

Lotze, M.T., and K. J. Tracey, "High-Mobility Group Box 1 Protein (HMGB1): Nuclear Weapon in the Immune Arsenal," *Nature Rev. Immunol.* 5:331-342 (2005).

Ma, W., et al. "Detection of Anti-Neutrophil Cytoplasmic Antibodies in MRL/Mp-*lpr/lpr* Mice and Analysis of Their Target Antigen," *Autoimmunity*, 32(4):281-291 (2000).

Maeda, S., et al., "Essential Roles of High-Mobility Group Box 1 in the Development of Murine Colitis and Colitis-Associated Cancer," *Biochemical and Biophysical Research Communications*, 360: 394-400 (2007).

Marks, J. D., et al., "By-Passing Immunization: Building High Affinity Human Antibodies by Chain Shuffling," *Bio/Technology*, 10:779-783 (1992).

Martin, M., et al., "Role of Innate Immune Factors in the Adjuvant Activity of Monophosphoryl Lipid A," *Infect. Immun.*, 71(5):2498-2507 (2003).

Matsuguchi, T., et al., "Gene Expressions of Toll-Like Receptor 2, But Not Toll-Like Receptor 4, Is Induced by LPS and Inflammatory Cytokines in Mouse Macrophages," *J. Immunol.*, 165(10): 5767-5772 (2000).

Means, T. K., et al., "Human Toll-Like Receptors Mediate Cellular Activation by *Mycobacterium tuberculosis*," *J. Immunol.*, 3920-3927 (1999).

Meldrum, D.R., "Tumor Necrosis Factor in the Heart," *Am. J. Physiol.* 274: R577-R595 (1998).

Melloni, E., et al., "Extracellular Release of the 'Differentiation Enhancing Factor', and a HMG1 Protein Type, is an Early Step in mUrine Erythroluekemia Cell Differentiation," *FEBS Lett.*, 368: 466-470 (1995).

Melloni, E., et al., "Identity in Molecular Structure Between "Differentiation Enhancing Factor" of Murine Erithroleukemia Cells and the 30 kD Heparin-Binding Protein of Developing Rat Brain," *Biochemical and Biophysical Research Communications*, 210(1): (1995).

Meng, G., et al., "Antagonistic antibody prevents toll-like receptor 2-driven lethal shocklike syndromes," *J. Clin. Invest.*, 113(1):1473-1481 (2004).

Meng, G., et al., "Murine TLR2 expression anaylsis and systemic antagonism by usage of specific monoclonal antibodies," *Immunology Letters*, 98:200-207 (2005).

Merenmies, J., et al., "30-kDa Heparin-Binding Protein of Brain(Amphoterin) Involved in Neurite Outgrowth," *J. Biol. Chem.*, 266(25): 16722-16729 (1991).

Milev, P., et al., "High Affinity Binding and Overlapping Localization of Neurocan and Phosphacan/Protein-Tyrosine Phosphatase-ζ/β with Tenascine-4, Amphoterine, and the Heparin-Binding Growth-Associated Molecule," *J. Biol. Chem.*, 273(12):6998-7005 (1998).

Miller, D.W. and Dill, Ken A., "Ligand binding to proteins: The binding landscape model," *Prot Sci*, 6:2166-2179 (1997).

Miyata, T., et al., "The Receptor for Advanced Glycation End Products (RAGE) is a Central Mediator of the Interaction of AGE-$\beta_2$Microglobulin With Human Mononuclear Phagocytes Via an Oxidant-Sensitive Pathway," *J. Clin. Invest.* 98(5):1088-1094 (1996).

Mohan, P.S., et al., "Sulfoglycolipids Bind to Adhesive Protein Amphoterin (p30) in the Nervous System," *Biochemical and Biophysical Research Communications*, 182(2) (1992).

Ohlin, M., et al., "Human Monoclonal Antibodies Against a Recombinant HIV Envelope Antigen Produced by Primary in vitro Immunization. Characterization and Epitope Mapping," *Immunology*, 68:325-331 (1989).

Ombrellino, M., et al., "Increased Serum Concentrations of High-Mobility-Group Protein 1 in Haemorrhagic Shock," *Lancet* 354 (9188):1446-1447 (1999).

Opal, S.M. and Huber, C.E., "Bench-To-Bedside Review: Toll-Like Receptors and Their Role in Septic Shock," *Crit. Care*, 6(2):125-136 (2002).

Østerud, B., et al., "Role of Monocytes in Atherogenesis," *Physiol. Rev.* 83(4):1069-1112 (2003).

Ozaki, S., "Identification of New P-ANCA, Correspondent Antigen," *Antigen, Inflammation and Immunity* 7(1):53-61 (1999).

Ozaki, S., "High Mobility Group Protein HMG1/HMG2: Clinical Significance of the Autoantibodies," *Jpn. J. Clin. Immun.*, 21(3)95-107 (1998).

Ozaki, S., et al., "Epitope Mapping of Autoantibodics to High Mobility Group (HMG) Proteins HMG1 and HMG2," *Clinical and Experimental Immunology* 120 suppl 1, p. 53 (May 2000).

Park, J.S. et al., "Involvement of Toll-like Receptors 2 and 4 in Cellular Activation bby High Mobility Group Box 1 Protein," *J. Biol. Chem.* 279(9):7370-77 (2004).

Parkinnen, J., et al. "Amphoterin, the 30-kDa Protein in a Family of HMG1-type Polypeptides," *J. Biol. Chem.*, 268(26):19726-19738 (1993).

Parkkinen, J., et al., "Interactions of Plasminogen and Tissue Plasminogen Activator (t-PA) with Amphoterin," *J. Biol. Chem.*, 266(25): 16730-16735 (1991).

Passalacqua, M., et al., "Stimulated Astrocytes Release High-Mobility Group 1 Protein, an Inducer of Lan-5 Neuroblastoma Cell Differentiation," *Neuroscience*, 82(4):1021-1028 (1998).

Patel, M., et al., "TLR2 Agonist Ameliorates Established Allergic Airway Inflammation by Promoting Th1 Response and Not via Regulatory T Cells," *J. Immunol*, 174:7558-7563 (2005).

Pedersen, D., et al., "The Role of Chromosomal HMGB proteins in Plants," *Biochimica et Biophysica Acta*, 1799:171-174 (2010).

(56) References Cited

OTHER PUBLICATIONS

Poltorak, A., et al., "Defective LPS Signaling in C3H/HeJ and C57BL/10ScCr Mice: Mutations in Tlr4 Gene," *Science* 282:2085-2088 (1998).

Popovic, K., et al., "Increased Expression of the Novel Proinflammatory Cytokine HMGB1 is Detected in Cutaneous Lupus Erythematosus Lesions," J. Investigative Dermatology 123(2): & 34th Annual Meeting of the European Society for Dermatological Research, Vienna, Austria, Sep. 2004.

Popovic, K., et al., "Increased Expression of the Novel Proinflammatory Cytokine High Mobility Group Box Chromosomal Protein 1 in Skin Lesions of Patients with Lupus Erythematosus," *Arthritis & Rheumatism*, 52(11): 3639-3645 (2005).

Rauvala, H. and Pihlaskari, R., "Isolation and Some Characteristics of an Adhesive Factor of Brain That Enhances Neurite Outgrowth in Central Neurons," *J. Biol. Chem.*, 262(34):16625-16635 (1987).

Rauvala, H., et al., "The Adhesive and Neurite-Promoting Molecule p30: Analysis of the Amino-Terminal Sequence and Production of Antipeptide Antibodies That Detect p30 at the Surface of Neuroblastoma Cells and of Brain Neurons," *J. Cell Biol.*, 107(6):2293-2305 (1988).

Redlitz, A., et al., "Receptors for Plasminogen and t-PA: An Update," *Baillière's Clinical Haemtology*, 8(2): 313-327 (1995).

Reeves, R. and Nissen, M.S., "The A•T-DNA-binding Domain of Mammalian High Mobility Group I Chromosomal Proteins," *J. Biol. Chem.*, 265(15):8573-8582 (1990).

Reeves, R., "Molecular Biology of HMGA Proteins: Hubs of Nuclear Function," *Gene* 277:63-81 (2001).

Riedemann, N.C., et al., "Novel Strategies for the Treatment of Sepsis," *Nature Med.*, 9(5):517-524 (2003).

Rogalla, P., et al., "Mapping and molecular characterization of five HMG1-related DNA sequences," *Cytogenet Cell Genet*, 83:124-129 (1998).

Romani, M., et al., "Serological Analysis of Species Specificity in the High Mobility Group Chromosomal Proteins," *J. Biol. Chem.*, 254(8):2918-2922 (1979).

Romine, L.E., et al., "The High Mobility Group Protein 1 Enhances Binding of the Estrogen Receptor DNA Binding Domain to the Estrogen Response Element," *Molecular Endocrinology* 12:664-674 (1998).

Sakamoto, R., et al., "Inhibitory Effect of Glycyrrhizin on the Phosphorylation and DNA-Binding Abilities of High Mobility Group Proteins 1 and 2 in Vitro," *Biol. Pharm. Bull.* 24(8):906-911 (2001).

Salmivirta, M., et al., "Neurite Growth-Promoting Protein (Amphoterin, p. 30) Binds Syndecan," *Exp. Cell Res.*, 200: 444-451 (1992).

Scaffidi, P., et al., "Release of chromatin protein HMGB1 by Necrotic Cells Triggers Inflammation," *Nature*, 418:191-95 (2002).

Schmidt, A.M., et al., "The Multiligand Receptor RAGE as a Progression Factor Amplifying Immune and Inflammatory Responses," *J. Clinical Investigation* 108(7):949-955 (Oct. 2001).

Shekelle, P., et al., "Effect of Supplemental Antioxidants Vitamin C, Vitamin E, and Coenzyme Q10 for the Prevention and Treatment of Cardiovascular Disease," AHRQ Evidence Reports, No. 83, Jul. 2003, [online] [retrieved on May 24, 2011]. Retrieved from the Internet: http://www.ncbi.nlm.nih.gov/books/NBK37059.

Sioud, M., et al., "Characterization of Naturally Occurring Autoantibodies Against Tumour Necrosis Factor-alpha (TNF-α): in vitro function and Precise Epitope Mapping by Phage Epitope Library," *Clin. Exp. Immunol.* 98:520-525 (1994).

Sjögren-Jansson, E., et al., "Production in Human Monoclonal Antibodies in Dialysis Tubing," *Hybridoma*, 10(3):411-419 (1991).

Sobajima, J., et al. "High Mobility Group (HMG) Non-histone Chromosomal Proteins HMG1 and HMG2 are Significant Target Antigens of Perinuclear Anti-Neutrophil Cytoplasmic Antibodies in Autoimmune Hepatitis," *Gut*, 44:867-873 (1999).

Sobajima, J., et al., "Anti-neutrophil cytopasmic antibodies (ANCA) in ulcerative colitis: anti-cathepsin G and a novel antibody correlate with a refractory type," *Clin. Exp. Immunol.*, 105:120-124 (1996).

Sobajima, J., et al., "Novel autoantigens of perinuclear anti-neutrophil cytoplasmic antibodies (P-ANCA) in ulcerative colitia: non-histone chromosomal proteins, HMG1 and HMG2," *Clin. Exp. Immunol.*, 107:135-140 (1997).

Sobajima, J., et al., "Prevalence and Characterization of Perinuclear Anti-Neutrophil Cytoplasmic Antibodies (P-ANCA) Directed Against HMG1 and HMG2 in Ulcerative Colitis (UC)," *Clin. Exp. Immunol.*, 111:402-407 (1998).

Sporatore, B., et al., "Extracellular high-mobility group 1 protein is essential for murine erythroleukaemia cell differentiation," *Biochem. J.*, 320:253-256 (1996).

Stedman's Medical Dictionary, 26th ed. (Baltimore, Williams & Wilkins) 1995, p. 283.

Straino, Stefania, et al., "High-Mobility Group Box 1 Protein in Human and Murine Skin: Involvement in Wound Healing," *J. of Investigative Dermatology* 10:1-9 (Jan. 2008).

Suda, T., et al., "A Novel Activity of HMG Domains: Promotion of the Triple-Stranded Complex Formation Between DNA Containing $(GGA/TCC)_{11}$ and $d(GGA)_{11}$ Oligonucleotides," *Nucleic Acids Res.*, 24(23):4733-4740 (1996).

Swiss-Prot Accession No. P09429, "High Mobility Group Protein 1 (HMG-1) (High Mobility Group Protein B1)," (2006) [online] [retrieved on Mar. 9, 2006], Retrieved from the Internet:<URL:http://www.ncbi.nlm.nih.gov>.

Tabeta, K. et al., "Toll-Like Receptors Confer Responsiveness to Lipopolysaccharide From *Porphyromonas gingivalis* in Human Gingival Fibroblasts," *Infect Immun.* 68(6):3731-3735 (2000).

Taguchi, A., et al., "Blockade of RAGE-amphoterin Signalling Suppresses Tumour Growth and Metastases," *Nature*, 405:354-360 (2000).

Taniguchi, N., et al., "High Mobility Group Box Chromosomal Protein 1 Plays a Role in the Pathogenesis of Rheumatoid Arthritis as a Novel Cytokine," *Arthritis Rheum.*, 48(4):971-981 (2003).

Taudte, S., et al., "Interactions Between HMG Boxes," *Protein Eng.*, 14(12):1015-1023 (2001).

Tomita, N., et al., "Direct in Vivo Gene Introduction into Rat Kidney," *Biochemical and Biophysical Research Communications*, 186 (1):129-134 (1992).

Toogood, G.J., et al., "The Immune Response following Small Bowel Transplantation," *Transplantation*, 62 (6):851-855 (1996).

Trilateral Project B3b, Mutual Understanding in Search and Examination, Report on Comparative Study on Biotechnology Patent Practices, Theme: Comparative Study on "Reach-Through Claims", pp. 1-19, European Patent Office, Japan Patent Office, United States Patent and Trademark Office, San Francisco, CA (2001).

Tsuda, K., et al., "Primary Structure of Non-Histone Protein HMG1 Revealed by the Nucleotide Sequence," *Biochemistry*, 27:6159-6163 (1988).

Tsuneoka, M., et al., "Monoclonal Antibody Against Non-Histone Chromosomal Protein High Mobility Group 1 Co-Migrates With High Mobility Group 1 Into the Nucleus," *J. Biol. Chem.*, 261(4):1829-1834 (1986).

Tsung, A., et al., "The Nuclear Factor HMGB1 Mediates Hepatic Injury After Murine Liver Ischemia-Reperfusion," *Journal of Experimental Medicine*, 201(7): 1135-1143 (2005).

Ueno, H., et al., "Contributions of High Mobility Group Box Protein in Experimental and Clinical Acute Lung Injury," *Am. J. Respir. Crit. Care Med.*, 170:13010-13016 (2004).

Uesugi, H., et al., "Prevalence and Characterization of Novel pANCA, Antibodies to the High Mobility Group Non-Histone Chromosomal Proteins HMG1 and HMG2, in Systemic Rheumatic Diseases," *J. Rheumatol.*, 25(4):703-709 (1998).

Vanderbilt, J.N., et al., "Monoclonal Antibodies as Probes for the Complexity, Phylogeny, and Chromatin Distribution of High Mobility Group Chromosomal Proteins 1 and 2," *J. Biol. Chem.*, 260(16):9336-9345 (1985).

Vassalli, J., et al., "The Plasminogen Activator/Plasmin System," *J. Clin. Invest.*, 88: 1067-1072 (1991).

Wang, H., et al., "HMG-1 as a Late Mediator of Endotoxin Lethality in Micc," *Science*, 285:248-251 (1999).

Wang, H., et al., "Proinflammatory Cytokines (Tumor Necrosis Factor and Interleukin 1) Stimulate Release of High Mobility Group Protein-1 by Pituicytes," *Surgery*, 126:389-392(1999).

(56) References Cited

OTHER PUBLICATIONS

Waterston, A.M. et al., "TNF Autovaccination Induces Self Anti-TNF Antibodies and Inhibits Metastasis in a Murine Melanoma Model," *Br. J. Cancer* 90(6):1279-84 (2004).
Watson, J.D., Recombinant DNA, $2^{nd}$ Ed. W.H. Freeman and Company pp. 127-130 (1997).
Weir, H.M., et al., "Structure of the HMG Box Motif in the B-Domain of HMG1," *EMBO Journal*, 12(4):1311-1319 (1993).
Wen, L., et al., "A Human Placental cDNA Clone that Encodes Nonhistone Chromosomal Protein HMG-1," *Nucleic Acids Res.*, 17(3):1197-1213 (1989).
Wisniewski, J.R., et al., "Region of Insect High Mobility Group (HMG)1 Protein Homologous of Helix 2 of the Rat HMG1-B Box is in Close Contact with DNA," *J. Biol. Chem.* 269(46):29261-29264 (1994).
Wood, R.F.M. and Pockley, A.J. review of Friend, P.J., et al., "Phase I Study of an Engineered Agycosylated Humanized CD3 Antibody in Renal Transplant Rejection," *Transplantation*, 68(10:1625-1626 (1999).
Xiang, Y., et al., "Expression of High-Mobility Group-1 mRNA in Human Gastrointestinal Adenocarcinoma and Corresponding Non-Cancerous Mucosa," *Int. J. Cancer* (Pred. Oncol.) 74:1-6 (1997).
Yakushijin, T., et al., "Reduced expression and functional impairment of Toll-like receptor 2 on dendritic cells in chronic hepatitis C virus infection," *Hepatology Research* 34:156-162 (2006).
Yamada, S., et al., "High Mobility Group Protein 1 (HMGB1) Quantified by ELISA With a Monoclonal Antibody That Does Not Cross-React With HMGB2," *Clin. Chem.*, 49(9):1535-1537 (2003).
Yamawaki, M., et al., "Generation and Characterization of Anti-Sulfoglucuronosyl Paragloboside Monoclonal Antibody NGR50 and its Immunoreactivity with Peripheral Nerve," *J. Neurosci. Res.*, 44: 586-593 (1996).
Yan, S.D., et al., "Amyloid-β Peptide-Receptor for Advanced Glycation Endproduct Interaction Elicits Neuronal Expression of Macrophage-Colony Stimulating Factor: A Proinflammatory Pathway in Alzheimer Disease," *Proc. Natl. Acad. Sci.* USA 94:5296-5301 (1997).
Yang H., et al., "HMG-1 Rediscovered as a Cytokine," *Shock* 15:247-53 (2001).
Yang, R-B., et al., "Signaling Events Induced by Lipopolysaccharide-Activated Toll-Like Receptor 2," *J. lmmunol.*, 163:639-643 (1999).
Yang, R-B., et al., "Toll-Like Receptor-2 Mediates Lipopolysaccharide-Induced Cellular Signalling," *Nature*, 395:284-288 (1998).
Yasuda, T., et al., "Significant Increase of Serum High-Mobility Group Box Chromosomal Protein 1 Levels in Patients with Severe Acute Pancreatitis," *Pancreas* 33(4): 359-363 (2006).
Yujiri, T., et al., "Increased Serum Levels of High-Mobility Group Box 1 Protein in Patients Who Developed Acute Graft-Versus-Host Disease After Allogeneic Hematopoietic Stem Cell Transplantation," *Euro. J. Haematol.*, 85:366-367 (2010).
Zhang, M. et al., "Tumor Necrosis Factor," in *The Cytokine Handbook*, (Academic Press Limited), Third Edition, pp. 517-547 (1998).
Zuany-Amorim, C., et al., "Toll-Like Receptors as Potential Therapeutic Targets for Multiple Diseases," *Nat. Rev. Drug Discov.*, 1:797-807 (2002).
Decision rejecting the opposition (Art. 101(2) EPC), Patent No. EP 1 165 110, dated Jun. 8, 2009.
International Search Report (ISR), PCT/US00/03583, mailed May 23, 2001.
Invitation to Pay Additional Fees, PCT/US2004/029527, mailed May 17, 2005.
Invitation to Pay Additional Fees, PCT/US2006/027053, mailed Feb. 7, 2007.
Notice of Opposition to a European Patent, Patent No. EP 1 165 110, dated Feb. 28, 2007.
Notification Concerning Transmittal of International Preliminary Report on Patentability (IPRP), with IPRP, PCT/US2004/029527, mailed Mar. 23, 2006.
Notification Concerning Transmittal of International Preliminary Report on Patentability (IPRP), with IPRP, PCT/US2006/027053, mailed Jan. 31, 2008.
Notification of Transmittal of the International Search Report (ISR) and the Written Opinion (WO) of the International Searching Authority, or the Declaration, with ISR and WO, PCT/US2004/029527, mailed Jul. 11, 2005.
Notification of Transmittal of the International Search Report (ISR) and the Written Opinion (WO) of the International Searching Authority, or the Declaration, with ISR and WO, PCT/US2006/027053, mailed May 15, 2007.
Notification of Transmittal of the International Search Report or the Declaration (ISR) with ISR, PCT/US02/15329, mailed Jun. 20, 2003.
Notification of Trasnmittal of International Preliminary Examination Report (IPER) with IPER, PCT/US02/15329, mailed Nov. 29, 2004.
Observations of the Patent Proprietor, Patent No. EP 1 165 110, dated Oct. 2007.
Partial European Search Report, EP05 07 7852, mailed Aug. 18, 2006.
Partial European Search Report, EP06 07 5291.2, mailed Jan. 22, 2007.
Provision of the minutes in accordance with Rule 124(4) EPC, Patent No. EP 1 165 110, dated Jun. 8, 2009.
Statement of Grounds of Appeal, Appeal No. T 1492/09-3304, Patent No. EP 1 165 110, dated Oct. 27, 2009.
Summons to attend oral proceedings pursuant to Rule 115(1) EPC, Patent No. EP 1 165 110, dated Dec. 3, 2008.
Suppl. Partial ESR (incomplete), EP 00 91 5762, mailed Jun. 4, 2002.
Suppl. Partial European Search Report, EP 02 73 6852, c.
Written Opinion (WO), PCT/US00/03583, mailed Oct. 31, 2001.
Written Opinion, PCT/US02/15329, mailed Jun. 20, 2003.
Abdulahad, D.A., et al., "HMGB1 in Systemic Lupus Erythematosus: its role in Cutaneous Lesions Development," *Autoimmunity Reviews*, 9:661-665 (2010).
Aicher, A., et al., Differential Role for p38 Mitogen-Activated Protein Kinase in Regulating CD40-Induced Gene Expression in Dendritic Cells and B Cells, *J Immunol*, 163:5786-5795 (1999).
Alisprantis, et al. "Cell Activation and Apoptosis by Bacterial Lipoproteins Through Toll-like Receptor-2," *Science* 285: 736-9 (1999).
An, L-L, et al., "Targeting Different Isoforms of HMGB1 Leads to Different Beneficial Effects in Preclinical Models of Sepsis and Inflammatory Arthritis (Abstract)," 94th Annual AAI Meeting. Miami Beach, FL, May 18-22, 2007. p. 1.
Arrighi, J. F., et al., "A critical role for p38 mitogen-activated protein kinase in the maturation of human blood-derived dendritic cells induced by lipopolysaccharide, TNF-alpha, and contactsensitizers," *J Immunol*, 166:3837-3845 (2001).
Balint, R.F., and Larrick, J.W., "Antibody Engineering by Parsimonious Mutagenesis," *Gene*, 137(1):109-118 (1993).
Banchereau, J., and Steinman, R.M., "Dendritic cells and the control of immunity," *Nature*, 392:245-252 (1998).
Barkauskaite, V., et al., "Translocation of the Novel Cytokine HMGB1 to the Cytoplasm and Extracellular Space Coincides With the Peak of Clinical Activity in Experimentally UV-induced Lesions of Cutaneous Lupus Erythematosus," *Lupus* 16:794-802 (2007).
Basu, S., et al., "Necrotic But Not Apoptotic Cell Death Releases Heat Shock Proteins, Which Deliver a Partial Maturation Signal to Dendritic Cells and Activate the NF-Kappa B Pathway," *International Immunology*, 12(11):1539-1546 (2000).
Bie, Liang-feng, et al, "Expression, Purification and Identification of the Human High Mobility Group-1 Protein Code Gene in *E. coli*," Abstract.(2003).
Bustin, M., and Reeves, R., "High-Mobility-Group Chromosomal Proteins: Architectural Components That Facilitate Chromatin Function," *Progress in Nucleic Acid Research and Molecular Biolog*, 54:35-100 (1996).
Bustin, M., et al., "Structural features of the HMG chromosomal proteins and their genes," *Biochimica Et Biophysica Acta*, 1049(3):231-243 (1990).
Cattaneo, A. and Biocca, S., "The Selection of Intracellular Antibodies," *TIBTECH*. 17:115-121 (1999).

(56) References Cited

OTHER PUBLICATIONS

Clark, G. J., et al., Expression of the RelB transcription factor correlates with the activation of human dendritic cells, *Immunology*, 98:189-196 (1999).

Coyle, A. J., "HMGB1—New Role for an Old Protein A Mediator of Inflammation and Autoimmune Disease (Presentation)," National Cancer Institute, Frederick, MD, pp. 1-32 (Jun. 21, 2007).

Demarco, R. A., et al., "Monocytes Promote Natural Killer Cell-Interferon Gamma Production in Response to the 'Endogenous Danger Signal HMGB 1," *Mol Immunol*, 42: 433-444 (2005).

De Smedt, T., et al., "Regulation of dendritic cell numbers and maturation of lipopolysaccharide in vivo," *J. Exp Med*, 184:1413-1424 (1996).

Dumitriu, I. E., et al., "Requirement of HMGB1 and RAGE for the Maturation of Human Plasmacytoid Dendritic Cells," *Eur.J.Immunol.*, 35(7): 2184-2190 (2005).

Fearon, D.T., and Locksley, R.M., "The Instructive Role of Innate Immunity in the Acquired Immune Response," *Science* 272:50-54 (1996).

Fu, P., et al., "Synthesis, Conformation, Receptor Binding and Biological Activities of Monobiotinylated Human Insulin-Like Peptide 3," *J Peptide Res*, 63:91-98 (2004).

Gallucci, S., and Matzinger, P., "Danger Signals: SOS to the Immune System," *Current Opinion in Immunology*, 13:114-119 (2001).

Gallucci, S., et al., "Natural Adjuvants: Endogenous Activators of Dendritic Cells," *Nature Medicine*, 5(11):1249-1255 (1999).

Goodwin, G. H., et al., "A new group of chromatin-associated proteins with a high content of acidic and basic amino acids," *European Journal of Biochemistry*, 38:14-19 (1973).

Harris, H.E. and Andersson, U. "Mini-review: The Nuclear Protein HMGB I as a Proinflammatory Mediator," *Eur J Immunol*, 34:1503-1512 (2004).

Hartmann, G., et al., "CpG DNA: A Potent Signal for Growth, Activation, and Maturation of Human Dendritic Cells," *Proc. Natl. Acad. Sci. USA*, 96:9305-9310 (1999).

Hatada, T., et al., "Plasma Concentrations and Importance of High Mobility Group Box Protein in the Prognosis of Organ Failure in Patients with Disseminated Intravascular Coagulation," *Thromb. Haemost.*, 94: 975-9 (2005).

Higashi, T., et al., "The Receptor for Advanced Glycation End Products Mediates the Chemotaxis of Rabbit Smooth Muscle Cells," *Diabetes* 46:463-472 (1997).

Huttunen, H. J., et al., "Receptor for Advanced Glycation End Products (RAGE)-Mediated Neurite Outgrowth and Activation of NF-kappaB Require the Cytoplasmic Domain of the Receptor But Different Downstream Signaling Pathways," *The Journal of Biological Chemistry*, 274(28):19919-19924 (1999).

Inaba, K., et al., "Generation of Large Numbers of Dendritic Cells From Mouse Bone Marrow Cultures Supplemented With Granulocyte/Macrophage Colony-Stimulating Factor," *J. Exp. Med.*, 176: 1693-1702 (1992).

Jantzen, H. M., et al., "Nucleolar Transcription Factor hUBF Contains a DNA-Binding Motif With Homology to HMG Proteins," *Nature*, 344:830-836 (1990).

Kokkola, R.., et al., "RAGE is the major receptor for the proinflammatory activity of HMGB 1 in rodent macrophages," *Scand J Immunol*, 61: 1-9 (2005).

Kolodrubetz, D., "Consensus Sequence for HMG1-Like DNA Binding Domains," *Nucleic Acids Res.*,18(8):5565 (1990).

Laudet, V., et al., "Ancestry and Diversity of the HMG Box Superfamily," *Nucleic Acids Res.*, 21(10): 2493-501 (1993).

Lamaitre, B., et al., "The Dorsoventral Regulatory Gene Cassett spätzle/Toll/cactus Controls the Potent Antifungal Response in *Drosophila* Adults," *Cell*, 86:973-983 (1996).

Lenschow, D.J., et al., "CD28/B7 System of T Cell Costimulation," *Annul Rev. Immunol.* 14: 233-258 (1996).

Majumdar, A., et al., "Sequence of Human HMG2 cDNA," *Nucleic Acids Res.*, 19: 6643 (1991).

Mao, S-Y, et al., "Antagonizing HMGB1 Inhibits Proteinuria in a Murine Model of Lupus-Like Disease (Abstract),", 94th Annual AAI Meeting. Miami Beach, FL, May 18-22, 2007. pp. 1.

Mao, S-Y, et al., "Antagonizing HMGB1 Blocks Inflammation and Tissue Damage in Experimental Arthritis," (Abstract and Presentation). ACR/ARHP 2007 Meeting. Boston, MA, Nov. 6-11, 2007. pp. 1-17.

Medzhitov, R., and Janeway, Jr., C.A., "Innate Immunity: Impact on the Adaptive Immune Response," *Curr. Opin. Immunol.*, 9:4-9 (1997).

Medzhitov, R., and Janeway, Jr., C.A., "Innate Immunity: The Virtues of a Nonclonal System of Recognition," *Cell*, 91:295-298 (1997).

Medzhitov, R., et al., "A human homologue of the *Drosophila* Toll protein signals activation of adaptive immunity," *Nature*, 388:394-397 (1997).

Messmer, D., et al., "Endogenously expressed nef uncouples cytokine and chemokine production from membrane phenotypic maturation in dendritic cells," *J Immunol*, 169:4172-4182 (2002).

Messmer, D, et al., "High Mobility Group Box Protein 1: An Endogenous Signal for Dendritic Cell Maturation and Th1 Polarization," *The Journal of Immunology*, 173:307-313, (2004).

Moron, G., et al., "New tools for Antigen Delivery to the MHC Class I Pathway," *Trends in Immunology*, 25(2):92-97 (2004).

Muller, S., et al., "Regulated Expression and Subcellular Localization of HMGB1, a Chromatin Protein with a Cytokine Function," *J. Intern. Med*, 255: 332-343 (2004).

Nagamine, T., et al., "Clinical evaluation of biotinbinding immunoglobulin in patients with Graves' disease," *Clin Chim Acta*, 226: 47-54 (1994).

Neumann, M., et al., "Differential expression of Rel/NF-kappB and octamar factors is a hallmark of the generation and maturation of dendtric cells," *Blood*, 95(1):277-285 (2000).

Osaki, T., et al., "Potent antitumor effects mediated by local expression of the mature form of the interferon-gamma inducing factor, interleukin-18 (1L- 1 8)," *Gene Ther*, 6: 808-815 (1999).

Ouaaz, F., et al., "A critical role for the Re1A subunit of nuclear factor kappaB in regulation of multiple immune-response genes and in Fas-induced cell death," *The Journal of Experimental Medicine*, 189:999-1004 (1999).

Padlan, E.A., "Anatomy of the Antibody Molecule," *Mol Immunol.*, 31(3):169-217 (1994).

Parrish, W., and Ulloa, L.,"High-Mobility Group Box-1 Isoforms as Potential Therapeutic Targets in Sepsis," *Methods in Molecular Biology*, 361(2):145-162(2007).

Portolano, S., et al., "Lack of Promiscuity in Autoantigen-Specific H and L Chain Combinations as Revealed by Human H and L Chain "Roulette,"" *J Immunol.*,150(3):880-887 (1993).

Pullerits, R., et al, "High mobility group box chromosomal protein 1, a DNA binding cytokine, induces arthritis," *Arthritis and Rheumatism*, 48(6):1693-1700 (2003).

Rescigno, M., et al., "Dendritic cell maturation is required for initiation of the immune response," *J. Leukocyte Biology*, 61:415-421 (1997).

Rescigno, M., et al., "Dendtritic cell survival and maturation are regulated by different signaling pathways," *J Exp Med*, 188(11):2175-2180 (1998).

Rock, F.L., et al. "A Family of Human Receptors Structurally Related to *Drosophila* Toll," *Proc. Natl. Acad. Sci.* USA, 95:588-593 (1998).

Rosenberg, A.M. and Cordeiro, D.M., "Relationship between Sex and Antibodies to High Mobility Group Proteins 1 and 2 in Juvenile Idiopathic Arthritis," *J. Rheumatol.*, 27: 2489-93 (2007).

Rovere-Querini, Patrizia, et al., "Environmental Adjuvants, Apoptosis and the Censhorship Over Autoimmunity," *Autoimmunity Reviews, Elsevier*, 4:555-560 (2005).

Sanford, A.N. et al., "Apoptotic Cells, Autoantibodies, and the Role of HMGB1 in the Subcellular Localization of an Autoantigen," *Journal of Autoimmunity*, Elsevier, 25:264-271 (2005).

Sato, K., et al., "Extracellular signal-regulated kinase, stress-activated protein kinase/c-Jun N-terminal kinase, and p3 8mapk are involved in IL-I 0-mediated selective repression of TNFalpha-induced activation and maturation of human peripheral blood monocyte-derived dendritic cells," *J Immunol*, 162:3865-3872 (1999).

(56) References Cited

OTHER PUBLICATIONS

Sauter, B., et al., "Consequences of cell death: exposure to necrotic tumor cells, but not primary tissue cells or apoptotic cells, induces the maturation of immunostimulatory dendritic cells," *The Journal of Experimental Medicine*, 191(3):423-433 (2000).
Schwandner, R., et al., "Peptidoglycan-and Lipoteichoic Acid-induced Cell Activation is Mediated by Toll-like Receptor 2," *J. Biol. Chem.*, 274(25):17406-17409 (1999).
Seshagiri, P.B., and Adiga, P.R., "Isolation and characterisation of a biotin-binding protein from the pregnant-rat serum and comparison with that from the chicken eggyolk," *Biochim Biophys Acta*, 916: 474-481 (1987).
Shirakawa, H., and Yoshida, M., "Structure of a Gene Coding for Human HMG2 Protein," *J.Biol.Chem.*, 267(10):6641-6645 (1992).
Tahara, H., and Lotze, M.T., "Antitumor effects of interleukin-12 (1L-12): applications for the immunotherapy and gene therapy of cancer," *Gene Ther*, 2: 96-106 (1995).
Telusma, G. et al., "Dendritic Cell Activiating Peptides Induce Distinct Cytokine Profiles," *International Immunology*, 18(11):1563-1573 (2006).
Thomas, J.O., and Travers, A.A., "HMG1 and 2, and Related 'Architectural' DNA-Binding Proteins," *Trends in Biochemical Sciences*, 26(3):167-74 (2001).
Tian, J., et al., "Toll-Like Receptor 9-Dependent Activation by DNA-Containing Immune Complexes is Mediated by HMGB1 and RAGE," *Nat. Immunol.*, vol. 8(5):487-496, (2007).
Tian, J., et al., "Regulation of TLR9 Dependent DNA Immune Complex Mediated Cell Activation by High Mobility Group Box Protein 1 (HMGB1) and Receptor for Advanced Glycation End Products (RAGE) (Abstract )", 94th Annual AAI Meeting. Miami Beach, FL, May 18-22, 2007. pp. 1.
Tian, J., et al., (Coyle presenter) "HMGB1—New Role for an Old Protein A Mediator of Inflammation and Autoimmune Disease," (Abstract and Presentation), *British Society of Biochemistry*, Cambridge, UK, Aug. 8-10, 2007 pp. 1-32.
Vajdos, F.F., et al., "Comprehensive Functional Maps of the Antigen-Binding Site of an Anti-ErbB2 Antibody Obtained With Shotgun Scanning Mutagenesis," *J. Mol. Biol.* 320:415-428 (2002).
Wang, H., et al., "HMGB1 as a late mediator of lethal systemic inflammation," *American Journal of Respiratory and Critical Care Medicine*, 164:1768-1773 (2001).
Williams, M.A. and Fukuda, M., "Accumulation of Membrane Glycoproteins in Lysomomes Requires a Tyrosing Residue at a Particular Position in the Cytoplamic Tail," *J. Cell Biol.* 111:955-966 (1990).
Winter, G. et al., "Making Antibodies by Phage Display Technology," *Annual Review of Immunology, Annual Reviews Inc.*, 12:433-455, Abstract (Jan. 1, 1994).
Wittemann, B., et al., "Autoantibodies to Nonhistone Chromosomal Proteins HMG-1 and HMG-2 in Sera of Patients with Juvenile Rheumatoid Arthritis," *Arthritis Rheum.*, 33(9):1378-83 (1990).
Yang, H., et al., "HMGB1 as a cytokine and therapeutic target," *J. Endotoxin Res.*, 8(6):469-472 (2002).
Yang, H., et al., "Reversing established sepsis with antagonists of endogenous high-mobility group box 1," *Proc Natl Acad Sci* USA, 101(1): 296-301 (2004).
Yoshimura, et al., "Cutting Edge: Recognition of Gram-Positive Bacterial Cell Wall Components by the Innate Immune System Occurs Via Toll-Like Receptor 2," *J. Immunol.*, 163:1-5 (1999).

Extended European search report, EP 10075469.6, dated Jul. 22, 2011.
Notification of Transmittal of the International Search Report and the Written Opinion of the International Searching Authority, or the Declaration for PCT/US2005/021691 mailed Feb. 12, 2008.
Notification Concerning Transmittal of International Preliminary Report on Patentability Chapter 1 of the Patent Cooperation Treaty for PCT/US2005/021691 mailed Apr. 10, 2008.
Notification of Transmittal of the International Search Report and the Written Opinion of the International Searching Authority, or the Declaration for PCT/US2005/037734 mailed Sep. 5, 2007.
MedImmune, Inc. International Preliminary Report on Patentability and Written Opinion of the International Searching Authority for PCT/US2005/037734 mailed Oct. 11, 2007.
The International Search Report and the Written Opinion of the International Searching Authority for PCT/US2006/061258 mailed May 29, 2008.
Notification Concerning Transmittal of International Preliminary Report on Patentability (Chapter I of the Patent Cooperation Treaty) for PCT/US2006/061258 mailed Jul. 10, 2008.
International Search Report and Written Opinion of the International Searching Authority for PCT/US2006/061257 mailed Dec. 21, 2007.
Notification Concerning Transmittal of International Preliminary Report on Patentability (Chapter I of the Patent Cooperation Treaty) for PCT/US2006/061257 mailed Mar. 5, 2009.
Supplementary European Search Report for European Application No. 05856833.8 mailed Jan. 7, 2009.
Supplementary European Search Report for European Application No. 05858252.9 mailed Aug. 4, 2009.
Supplementary European Search Report for European Application No. 06848798.2 mailed Nov. 24, 2009.
Damschroder, M.M., et al, "Analysis of human and primate CD2 molecules by protein sequence and epitope mapping with anti-human CD2 antibodies," *Molecular Immunology* 41:985-1000 (2004).
Harlow, E., Using Antibodies: A Laboratory Manual, "Antibodies are useful reagents that can bind with high affinity to chosen antigens," Cold Spring Harbor Laboratory Press, p. 4 (1999).
Köhler, G. and Milstein, C., "Continuous cultures of fused cells secreting antibody of predefined specificity," Nature 256:495-497 (1975).
Voet, D., et al., Biochemistry, Section 6-3, Chemical Evolution, John Wiley & Sons, Inc., pp. 126-128 and 228-334 (1990).
Messmer, D., et al., "Human immunodeficiency virus type 1 Nef mediates activation of STAT3 in immature dendtritic cells", *AIDS Res Hum Retroviruses*, 18(14):1043-1050 (2002).
Mikayama, T., et al., "Molecular cloning and functional expression of a cDNA encoding glycosylation-inhibiting factor," *Proc. Natl. Acad. Sci.* USA 90:10056-10060 (1993).
Wang, H., et al., "Extracellular Role of HMGB1 in Inflammation and Sepsis", *J. Intern Med.*, 255:320-31 (2004).
Bianchi, M. E., et al., "Specific Recognition of Cruciform DNA by Nuclear Protein HMG1," *Science*, 243: 1056-1059 (1989).
Bianchi, M. E., and Manfredi, A. A., "High-mobility group box 1 (HMGB1) protein at the crossroads between innate and adaptive immunity," *Immunological Reviews*, 220: 35-46 (2007).
Rudikoff, S., et al., "Single amino acid substitution altering antigen-binding specificity," *PNAS*, 79(6): 1979-1983 (1982).
Tamura, M., et al., "Structural Correlates of an Anticarcinoma Antibody: Identification of Specificity-Determining Residues (SDRs) and Development of a Minimally Immunogenic Antibody Variant by Retention of SDRs Only," *J. Immunol.*, 164(3): 1432-1441 (2000).

* cited by examiner

HMG1 ANTIBODY FOR TREATING INFLAMMATORY CONDITIONS

RELATED APPLICATIONS

This application is a continuation of U.S. application Ser. No. 12/496,333, filed Jul. 1, 2009 now U.S. Pat. No. 8,138, 141, (allowed) which is a divisional of U.S. application Ser. No. 11/477,835, filed Jun. 29, 2006, now issued as U.S. Pat. No. 7,572,446, which is continuation of U.S. application Ser. No. 10/210,747, filed Jul. 31, 2002, now issued as U.S. Pat. No. 7,097,838, which is a continuation of U.S. application Ser. No. 09/503,632, filed Feb. 14, 2000, now issued as U.S. Pat. No. 6,468,533, which is a divisional of U.S. application Ser. No. 09/248,574, filed Feb. 11, 1999, now issued as U.S. Pat. No. 6,303,321. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 32681000038SEQ.txt; created 2-22-12, 1.36 KB in size.

TECHNICAL FIELD OF THE INVENTION

The present invention provides a pharmaceutical composition and method for treating diseases characterized by activation of an inflammatory cytokine cascade, particularly sepsis, including septic shock and ARDS (acute respiratory distress syndrome), comprising administering an effective amount of an antagonist to the high mobility group 1 protein (HMG1). The present invention further provides a diagnostic method for monitoring the severity of sepsis and related conditions, comprising measuring the serum concentration of HMG1 in a patient exhibiting symptoms of a disease characterized by activation of inflammatory cytokine cascade. Lastly, the present invention provides a pharmaceutical composition and method for effecting weight loss or treating obesity, comprising administering an effective amount of an HMG1 protein or a therapeutically active fragment of the gene product of an HMG1 gene.

BACKGROUND OF THE INVENTION

Sepsis is an often fatal clinical syndrome that develops after infection or injury. Sepsis is the most frequent cause of mortality in hospitalized patients. Experimental models of gram negative sepsis based on administration of bacterial endotoxin (lipopolysaccharide, LPS) have led to an improved understanding of the pathogenic mechanisms of lethal sepsis and conditions related to sepsis by virtue of the activation of a common underlying inflammatory cytokine cascade. This cascade of host-response mediators include TNF, IL-1, PAF and other macrophage-derived factors that have been widely studied as acute, early mediators of eventual lethality in severe endotoxemia (Zhang and Tracey, in *The Cytokine Handbook*, 3$^{rd}$ ed. Ed. Thompson (Academic Press Limited, USA). 515-547, 1998).

Unfortunately, therapeutic approaches based on inhibiting these individual "early" mediators of endotoxemia have met with only limited success in large prospective clinical trials against sepsis in human patients. It is possible to infer from these disappointing results that later-appearing factors in the host response might critically determine pathogenesis and/or lethality in sepsis and related disorders. Accordingly, there is a need to discover such putative "late" mediators necessary and/or sufficient for part or all of the extensive multisystem pathogenesis, or for the lethality, of severe endotoxemia, particularly as endotoxemia is representative of clinical sepsis and related clinical disorders.

HMG1 is a 30 kDa chromosomal nucleoprotein belonging to the burgeoning high mobility group (HMG) of non-histone chromatin-associated proteins. As a group, the HMG proteins recognize unique DNA structures and have been implicated in diverse cellular functions, including determination of nucleosome structure and stability, as well as in transcription and/or replication. The HMG proteins were first characterized by Johns and Goodwin as chromatin components with a high electrophoretic mobility in polyacrylamide gels (see in *The HMG Chromosomal Proteins*, E. W. Johns, Academic Press, London, 1982). Higher eukaryotes exhibit three families of HMG proteins: the HMG-1/-2 family, the HMG-14/-17 family and the HMG-I/-Y family. Although the families are distinguishable by size and DNA-binding properties, they are similar in their physical properties. HMG proteins are highly conserved across species, ubiquitously distributed and highly abundant, and are extractable from chromatin in 0.35 M NaCl and are soluble in 5% perchloric or trichloroacetic acid. Generally, HMG proteins are thought to bend DNA and facilitate binding of various transcription factors to their cognate sequences, including for instance, progesterone receptor, estrogen receptor, HOX proteins, and Oct1, Oct2 and Oct6. Recently, it has become apparent that a large, highly diverse group of proteins including several transcription factors and other DNA-interacting proteins, contain one or more regions similar to HMG1, and this feature has come to be known as the HMG1 box or HMG1 domain. cDNAs coding for HMG1 have been cloned from human, rat, trout, hamster, pig and calf cells, and HMG1 is believed to be abundant in all vertebrate cell nuclei. The protein is highly conserved with interspecies sequence identities in the 80% range. In chromatin, HMG1 binds to linker DNA between nucleosomes and to a variety of non-β-structures such as palindromes, cruciforms and stem-loop structures, as well as cisplatin-modified DNA. DNA binding by HMG1 is generally believed to be sequence insensitive. HMG1 is most frequently prepared from washed nuclei or chromatin, but the protein has also been detected in the cytoplasm. (Reviewed in Landsman and Bustin, *BioEssays* 15:539-546, 1993; Baxevanis and Landsman, *Nucleic Acids Research* 23:514-523, 1995). To date, no link has been established between the HMG proteins and any clinical condition or disease.

HMG1 has been alternatively identified as a heparin-binding protein abundantly expressed in developing brain and dubbed "amphoterin" for its highly dipolar sequence, comprising two internal repeats of a positively charged domain of about 80 amino acids (the HMG1 box) and an acidic C-terminal domain containing a stretch of approximately 30 continuous glutamic or aspartic acid residues. Amphoterin/HMG1 has been localized to the outer surface of the plasma membranes of epithelial, and especially neuronal cells, where it has been specifically localized to the filipodia of neural cells. Inhibition studies have suggested that amphoterin/HMG1 is required for process (neurite) extension and amphoterin/HMG1 also may be involved in neuron-glia interactions (Merenmies et al., *J. Biol. Chem.* 266:16722-16729, 1991; Milev et al., *J. Biol. Chem.* 273:6998-7005, 1998; and Salmivirta et al., *Exp. Cell Res.* 200:444-451, 1992). Amphoterin/HMG1 can be released from murine erythroleukemia cells after stimulation with the chemical inducer hexamethylenebisacetamide (Melloni et al., *Biochem. Biophys. Res. Commun.* 210:82-89, 1995). Previous study suggested that the gene product of the HMG1 gene functions as a differentiation enhancing factor by stimulating α-PKC (Melloni et al., *Biochem. Biophys. Res. Commun.* 210:82-89, 1995; and Melloni et al., *FEBS Lett.* 368:466-470, 1995).

The HMG1 gene product has been shown to interact with plasminogen and tissue-type plasminogen activator (t-PA) and effectively enhance plasmin generation at the cell surface, a system that is known to play a role in extracellular proteolysis during cell invasion and tissue remodeling. Amphoterin/HMG1 has also been shown to interact with the receptor of advanced glycosylation end products (RAGE) (Mohan et al., *Biochem. Biophys. Res. Commun.* 182:689-696, 1992; Yamawaki et al., *J. Neurosci. Res.* 44:586-593, 1996; Salmivirta et al., *Exp. Cell Res.* 200:444-451, 1992; and Vassalli et al., *J. Clin. Invest.* 88:1067-1072, 1991), (Redlitz and Plow, *Baillieres Clin. Haematol.* 8:313-327, 1995; and Parkkinen et al., *J. Biol. Chem.* 266:16730-16735, 1991).

There is a longstanding need in the art to discover improved agents that can prevent the cytokine-mediated inflammatory cascade and have therapeutic activity in a large variety of cytokine-mediated inflammatory diseases. The present invention was made during the course of investigative research to identify agents that mediate toxicity, pathogenesis and/or lethality in sepsis and other disorders related by a common activation of the inflammatory cytokine cascade.

Diseases and conditions mediated by the inflammatory cytokine cascade are numerous. Such conditions include the following grouped in disease categories:

Systemic Inflammatory Response Syndrome, which includes:
 Sepsis syndrome
 Gram positive sepsis
 Gram negative sepsis
 Culture negative sepsis
 Fungal sepsis
 Neutropenic fever
 Urosepsis
 Meningococcemia
 Trauma hemorrhage
 Hums
 Ionizing radiation exposure
 Acute pancreatitis
 Adult respiratory distress syndrome (ARDS)
 Reperfusion Injury, which includes
 Post-pump syndrome
 Ischemia-reperfusion injury
 Cardiovascular Disease, which includes
 Cardiac stun syndrome
 Myocardial infarction
 Congestive heart failure
 Infectious Disease, which includes
 HIV infection/HIV neuropathy
 Meningitis
 Hepatitis
 Septic arthritis
 Peritonitis
 Pneumonia Epiglottitis
 *E. coli* 0157:H7
 Hemolytic uremic syndromic/thrombolytic thrombocytopenic purpura
  Malaria
  Dengue hemorrhagic fever
  Leishmaniasis
  Leprosy
  Toxic shock syndrome
  *Streptococcal* myositis
  Gas gangrene
  *Mycobacterium* tuberculosis
  *Mycobaclerium avium intracellulare*
  *Pneumocystis carinii* pneumonia
  Pelvic inflammatory disease
  Orchitis/epidydimitis
  *Legionella*
  Lyme disease
  Influenza A
  Epstein-Barr Virus
  Virul associated hemiaphagocytic syndrome
  Viral encephalitis/aseptic meningitis
 Obstetrics/Gynecology, including:
  Premature labor
  Miscarriage
  Infertility
 Inflammatory Disease/Autoimmunity, which includes:
  Rheumatoid arthritis/seronegative arthropathies
  Osteoarthritis
  Inflammatory bowel disease
  Systemic lupus erythematosis
  Iridoeyelitis/uveitistoptic neuritis
  Idiopathic pulmonary fibrosis
  Systemic vasculitis/Wegener's gramilornatosis
  Sarcoidosis
  Orchitis/vasectomy reversal procedures
 Allergic/Atopic Diseases, which includes:
  Asthma
  Allergic rhinitis
  Eczema
  Allergic contact dermatitis
  Allergic conjunctivitis
  Hypersensitivity pneumonitis
 Malignancy, which includes:
  ALL
  AML
  CML
  CLL
  Hodgkin's disease, non-Hodgkin's lymphoma
  Kaposi's sarcoma
  Colorectal carcinoma
  Nasopharyngeal carcinoma
  Malignant histiocytosis
  Paraneoplastic syndrome/hypercalcemia of malignancy
 Transplants, including:
  Organ transplant rejection
  Graft-versus-host disease
  Cachexia
 Congenital, which includes:
  Cystic fibrosis
   Familial hematophagocytic lymphohistiocytosis
   Sickle cell anemia
 Dermatologic, which includes:
  Psoriasis
  Alopecia
 Neurologic, which includes:
  Multiple sclerosis
  Migraine headache
 Renal, which includes:
  Nephrotic syndrome
  Hermodialysis
  Uremia
 Toxicity, which includes:
  OKT3 therapy
  Anti-CD3 therapy
  Cytokine therapy Chemotherapy
Radiation therapy
Chronic salicylate intoxication
Metabolic/Idiopathic, which includes:
Wilson's disease
Hemachromatosis
Alpha-lantitrypsin deficiency
Diabetes
Hashimoto's thyroiditis
Osteoporosis
Hypothalamic-pituitary-adrenal axis evaluation
Primary biliary cirrhosis

SUMMARY OF THE INVENTION

The present invention provides a pharmaceutical composition for treating conditions (diseases) mediated by the inflammatory cytokine cascade, comprising an effective among of an antagonist or inhibitor of HMG1. Preferably, the HMG1 antagonists is selected from the group consisting of antibodies that bind to an HMG1 protein, HMG1 gene antisense sequences and HMG1 receptor antagonists. The present invention provides a method for treating a condition mediated by the inflammatory cytokine cascade, comprising administering an effective amount of an HMG1 antagonist. In another embodiment, the inventive method further comprises administering a second agent in combination with the HMG1 antagonist, wherein the second agent is an antagonist of an early sepsis mediator, such as TNF, IL-1α, IL-1β, MIF or IL-6. Most preferably, the second agent is an antibody to TNF or an IL-1 receptor antagonist (IL-1ra).

The present invention further provides a diagnostic and prognostic method for monitoring the severity and predicting the likely clinical course of sepsis and related conditions for a patient exhibiting shock-like symptoms or at risk to exhibit symptoms associated with conditions mediated by the inflammatory cascade. The inventive diagnostic and prognostic method comprises measuring the concentration of HMG1 in a sample, preferably a serum sample, and comparing that concentration to a standard for HMG1 representative of a normal concentration range of HMG1 in a like sample, whereby higher levels of HMG1 are indicative of poor prognosis or the likelihood of toxic reactions. The diagnostic method may also be applied to other tissue or fluid compartments such as cerebrospinal fluid or urine. Lastly, the present invention provides a pharmaceutical composition and method for effecting weight loss or treating obesity, comprising administering an effective amount of HMG1 or a therapeutically active fragment thereof.

BRIEF DESCRIPTION OF THE DRAWINGS

FIG. 1 shows two graphs that profile the induction of HMG1 release by LPS in vitro (FIG. 1A) and in vivo (FIG. 1B). Specifically.

FIG. 2 illustrates that HMG1 is a mediator of pathogenesis and lethality in endotoxemia.

FIG. 3 shows that HMG1 induced TNF release both in vitro (FIG. 3A) and in vivo (FIG. 3B). Specifically, FIG. 3A shows the mean±S.E.M. of the induced TNF response in two experiments (in triplicate).

FIG. 4 shows the mean±S.E.M. of net body weight change of three mice per group.

DETAILED DESCRIPTION OF THE INVENTION

Figure 1A:
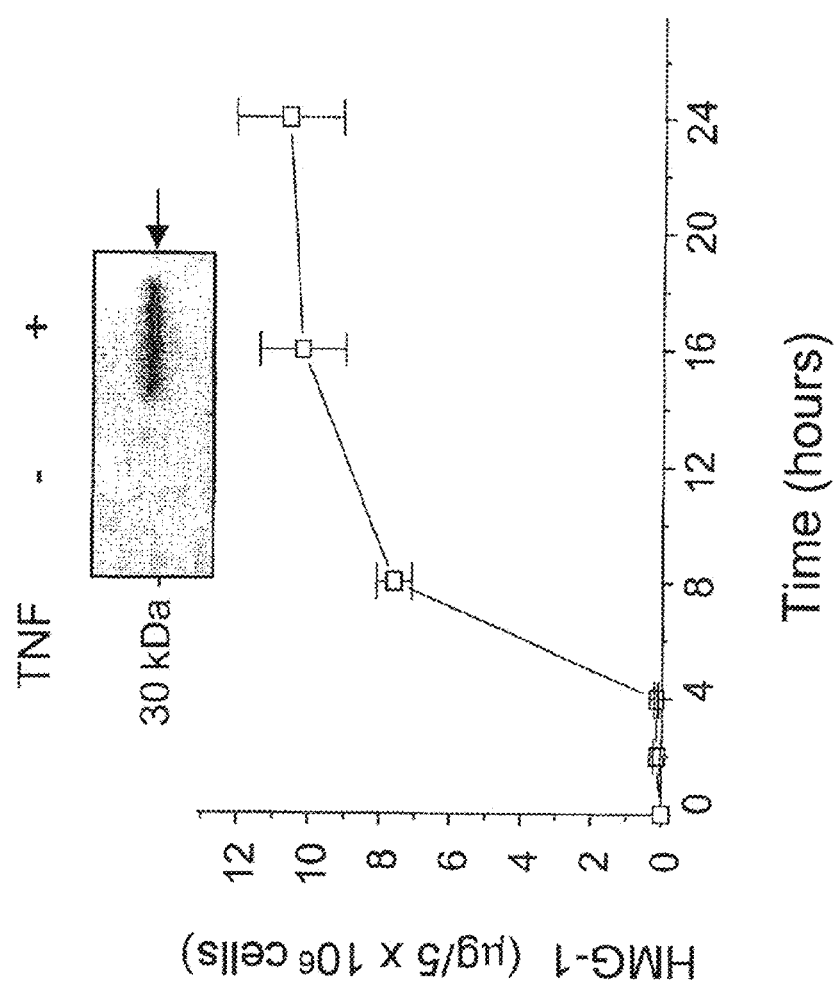
FIG. 1A shows the accumulation of HMG1 in culture supernatants of macrophage RAW 264.7 cells after stimulation with LPS (100 ng/ml). The inset is a Western blot (using antibodies raised against recombinant HMG1) showing induction of HMG1 release from RAW 264.7 cells after induction with TNF.

The present invention is based upon the discovery and isolation of a highly inducible 30 kDa protein that is released by, and accumulates in media conditioned by, cultured murine macrophage-like cells (RAW 264.7) following stimulation with LPS, TNF, or IL-1. A partial amino acid sequence of this isolated polypeptide was identical to the sequence of the HMG1 protein, also known as amphoterin, a protein not before linked to the pathogenesis of any disease. This information was used to clone a cDNA encoding HMG1, which sequence was expressed to provide recombinant protein, which protein was used to generate specific anti-HMG1 antibodies.

Therapeutic and diagnostic efficacy was determined in a series of predictive in vitro and in vivo experiments. The experiments are detailed in the Examples section. For example, following administration of endotoxin ($LD_{100}$) to mice, serum HMG1 levels increased later (at 16 h) than well-known "early" mediators of sepsis (such as TNF and IL-1) and plateau levels of HMG1 were maintained for 16 to 32 hours. Patients with lethal sepsis had high serum HMG1 levels, which were not detected in normal healthy volunteers. Moreover, acute experimental administration of rHMG1 to test animals, whether alone or in combination with sub-lethal amounts of LPS, caused marked pathological responses and even death. More distributed dosing schedules of lower amounts of rHMG1 led to significant weight loss in treated animals. These results give evidence that HMG1 is a mediator of endotoxemia and particularly a late mediator, as opposed to known "early" mediators such as TNF and IL-1. These data further show the importance of serum HMG1 as a marker for the severity or potential lethality of sepsis and related conditions.

In addition, treatment with anti-HMG1 antibodies provided full protection from $LD_{100}$ doses of LPS in mice. HMG1 is inducible by TNF and IL-1β, and dose-dependently stimulates TNF release from huPBMCs. TNF is a marker of macrophage activation, so it is likely (without limitation as to implied mechanisms or being bound by theory) that HMG1 promotes downstream re-activation of cytokine cascades which, in turn, mediates late pathogenesis and lethality in sepsis and related conditions involving activation of pro-inflammatory cytokine responses. Thus, HMG1 likely occupies a central role in mediating the inflammatory response to infection and injury, and antagonists of HMG1 will be of therapeutic benefit in sepsis and related conditions of inflammatory cascade activation. The appearance of HMG1 in the inflammatory cytokine cascade is suitable to propagate later phases of the host response and contribute to toxicity and lethality. The predictive data provided herein support the therapeutic efficacy of HMG1 antagonists and provide evidence in support of the aforementioned theory regarding mechanism of action. The in vivo treatment data showed the efficacy of HMG1 antagonists in general, and anti-HMG1 antibodies in particular, for treating conditions mediated by the inflammatory cytokine cascade in general and particularly sepsis conditions, including, for example, septic shock, sepsis syndrome or other "sepsis-like" conditions mediated by inflammatory cytokines. Further, the independent pathogenicity and toxicity/lethality of HMG1 shows that HMG1 antagonists are particularly effective when co-administered with antagonists of "early" inflammatory mediators such as TNF, MIF, IL-1 and IL-6.

In summary, HMG1 is a cytokine mediator of inflammatory reactions because: 1) HMG1 is released from macrophages and pituicytes following stimulation with bacterial toxins or with pro-inflammatory cytokines (TNF or IL-1β); 2) HMG1 accumulates in serum of animals exposed to LPS and in patients with sepsis; and 3) HMG1-specific antibodies protect against mortality in a predictive lethal endotoxemia animal model of clinical sepsis and related conditions.

Pharmaceutical Composition and Method of Administration

The inventive pharmaceutical composition or inventive pharmaceutical combination can be administered to a patient either by itself (complex or combination) or in pharmaceutical compositions where it is mixed with suitable carriers and excipients. The inventive pharmaceutical composition or inventive pharmaceutical combination can be administered parenterally, such as by intravenous injection or infusion, interperitoneal injection, subcutaneous injection, or intramuscular injection. The inventive pharmaceutical composition or inventive pharmaceutical combination can be administered orally or rectally through appropriate formulation with carriers and excipients to form tablets, pills, capsules, liquids, gels, syrups, slurries, suspensions and the like. The inventive pharmaceutical composition or inventive pharmaceutical combination can be administered topically, such as by skin patch, to achieve consistent systemic levels of active agent. The inventive pharmaceutical composition or inventive pharmaceutical combination can be formulated into topical creams, skin or mucosal patches, liquids or gels suitable for topical application to skin or mucosal membrane surfaces. The inventive pharmaceutical composition or inventive pharmaceutical combination can be administered by inhaler to the respiratory tract for local or systemic treatment.

The dosage of the inventive pharmaceutical composition or inventive pharmaceutical combination of the present invention can be determined by those skilled in the art from this disclosure. The pharmaceutical composition or inventive pharmaceutical combination will contain an effective dosage (depending upon the route of administration and pharmacokinetics of the active agent) of the inventive pharmaceutical composition or inventive pharmaceutical combination and suitable pharmaceutical carriers and excipients, which are suitable for the particular route of administration of the formulation (i.e., oral, parenteral, topical or by inhalation). The active agent is mixed into the pharmaceutical formulation by means of mixing, dissolving, granulating, dragee-making, emulsifying, encapsulating, entrapping or lyophilizing processes. The pharmaceutical formulations for parental administration include aqueous solutions of the active agent or combination in water-soluble form. Additionally, suspensions of the active agent may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the active agent or combination to allow for more concentrated solutions.

Pharmaceutical formulations for oral administration can be obtained by combining the active agent with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a disintegrating agent may be added, and a stabilizer may be added.

Antisense Oligomers

The present invention provides antisense oligomers having a sequence effective to inhibit or block the expression of the HMG1 gene or mRNA sequence. Antisense technology, which uses specific-oligonucleotides to inhibit expression of target gene products, is developing as a therapeutic modality for human disease. Several selection criteria are available to contribute to the optimization of antisense oligonucleotide antagonists. For example, it is advisable to choose sequences with 50% or more GC content. Preferred sequences span the AUG initiation codon of the target protein, but sites in the coding region and 5' UTR may perform equally well. Such sequences are generally about 18-30 nucleotides long and chosen to overlap the ATG initiation codon from the HMG1 cDNA sequence to inhibit protein expression. Longer oligomers are often found to inhibit the target to a greater extent, indicating that a preferred length is about 25 mer for the first oligonucleotides chosen as antisense reagents. Typically, three oligonucleotide sequences are chosen with regard to these criteria, and compared for antagonist activity to control oligonucleotide sequences, such as "reverse" oligonucleotides or those in which about every fourth base of the antisense sequence is randomized. Therefore, a preferred sequence for making antisense oligomer sequences to HMG1 is a 25 mer sequence chosen to overlap the ATG initiation codon (underlined) from the HMG1 cDNA sequence: GAG-GAAAAATAACTAAAC ATGGGCAAAGGAGATCCTAAGAGG [SEQ ID NO:5] and such preferred antisense sequences are used to construct antisense oligonucleotide agents (and suitable controls) for an in vitro comparison as antagonists of HMG1. These in vitro data are predictive of human clinical utility using antisense agents of comparable design.

HMG1-Directed Antibodies

The antibodies disclosed herein may be polyclonal or monoclonal; may be from any of a number of human, non-human eukaryotic, cellular, fungal or bacterial sources; may be encoded by genomic or vector-borne coding sequences; and may be elicited against native or recombinant HMG1 or fragments thereof with or without the use of adjuvants, all according to a variety of methods and procedures well-known in the art for generating and producing antibodies. Generally, neutralizing antibodies against HMG1 (i.e., those that inhibit biological activities of HMG1 particularly with regard to its pro-inflammatory cytokine-like role) are preferred for therapeutic applications while non-neutralizing antibodies may be as suitable for diagnostic applications. Examples of such useful antibodies include but are not limited to polyclonal, monoclonal, chimeric, single-chain, and various human or humanized types of antibodies, as well as various fragments thereof such as Fab fragments and fragments produced from specialized expression systems.

Diagnostic Assay

The diagnostic assay provided here uses anti-HMG1 antibodies that can be either polyclonal or monoclonal or both. The diagnostic procedure can utilize standard antibody-based techniques for measuring concentrations of the gene product of HMG1 genes in a biological fluid. Preferred standard diagnostic procedures are ELISA assays and Western techniques.

Example 1

Identification of HMG1 as a "Late" Mediator of Endotoxemia

This example provides the results of an experiment to identify and isolate later released macrophage-derived factors that play a role in sepsis and in related conditions typified by inflammatory cytokine activity. The experiment reported in this example examined murine macrophage RAW 264.7 cell-conditioned media after stimulation of the cultures with TNF. Murine macrophage RAW 264.7 cells were obtained from American Type Culture Collections (ATCC, Rockville, Md., USA), and proliferated in culture under DMEM supplemented with 10% fetal bovine serum and 1% glutamine. When confluency reached 70-80%, the medium was replaced by serum-free OPTI-MEM I medium and cultures were stimulated with pro-inflammatory cytokines (e.g., TNFα or IL-1) or bacterial endotoxin (LPS).

The proteins released from the above stimulated macrophage cultures were surveyed. Specifically, at different time points, cells and cell-conditioned media were separately collected by centrifugation (3000 rpm, 10 minutes). Proteins in the conditioned mediam were concentrated by ultrafiltration over Amicon membranes with Mr cutoff of 10 kDa (Amicon Inc., Beverly, Mass., USA), subsequently fractionated by SDS-PAGE, and stained with Coomassie blue (1.25% Coomassie Blue R250 in 30% methanol/10% acetic acid). After destaining with 30% methanol/7% acetic acid, protein(s) of interest (i.e., those that preferentially accumulated in conditioned media of stimulated cultures) was isolated by excision from the SDS-PAGE gel, and subjected to N-terminal sequencing analysis (Commonwealth Biotechnologies, Inc., Richmond, Va., USA).

Comparison of SDS-PAGE gel analysis of profiles of proteins accumulated in control (without TNFα stimulation) versus TNF-stimulated RAW 264.7 cells revealed a strongly inducible 30 kDa protein whose concentration in the cell-conditioned medium was significantly increased after stimulation for 16 hours. Amino acid sequence analysis of this isolated protein revealed its N-terminal sequence as Gly-Lys-Gly-Asp-Pro-Lys-Lys-Pro-Arg-Gly-Lys-Met-Ser-Ser [SEQ ID NO. 1]. A review of relevant gene databases found a 100% identity to the N-terminal amino acid sequence of HMG1.

These data identified HMG1 as a "late-appearing" product of LPS-stimulated macrophage cultures, and therefore as a candidate pro-inflammatory mediator. This activity was confirmed by administration of recombinantly produced HMG1 and/or of anti-HMG1 antibodies in cellular and animal model systems that are predictive of human clinical conditions.

Example 2

Cellular Sources of HMG1

This example shows which cell sources are capable of releasing HMG1 in response to TNF, IL-1 and/or LPS. Cells studied include $GH_3$ pituicytes, murine macrophage RAW 264.7 cells, human primary peripheral blood mononuclear cells (huPBMCs), human primary T cells, rat adrenal PC-12 cells, and rat primary kidney cells (Table 1). The rat pituitary $GH_3$ cell line was obtained from American Type Culture Collection (ATCC, Rockville, Md., USA), and cultured in DEME supplemented with 10% fetal bovine serum and 1% glutamine. Human PBMCs and T cells were freshly isolated from whole blood of healthy donors and cultured in RPMI 1640 supplemented with 10% human serum as previously described (Zhang, et al., J. Exp. Med. 185:1759-1768, 1997). When confluency reached 70-80% the medium was replaced by serum-free OPTI-MEM I medium and cultures stimulated with proinflammatory cytokines (e.g., TNFα or IL-1) or bacterial endotoxin (LPS).

Although human T cell, rat adrenal (PC-12) cells, and rat primary kidney cells contained cell-associated HMG1 as demonstrated by Western blotting analysis of whole cell lysates using HMG1-specific antibodies (see example 4 below), HMG1 did not significantly accumulate in the medium of these cultures after stimulation with either TNF, IL-1β, or LPS (Table 1).

TABLE 1

Induced release of HMG1 from various types of cells.

|  | Stimulus | | |
| --- | --- | --- | --- |
| Cell Type | TNF | IL-1β | LPS |
| Murine RAW 264.7 cells | Yes | Yes | Yes |
| Human PBMCs | Yes | Yes | Yes |
| Human primary T cells | No | No | No |
| Rat adrenal PC-12 cells | No | No | No |
| Rat pituitary $GH_3$ cells | Yes | Yes | No |
| Rat primary kidney cells | No | No | No |

Note:
PBMCs, peripheral blood mononuclear cells.

TNF, IL-1β (minimal effective concentration=5 ng/ml for each) and bacterial endotoxin (LPS, minimal effective concentration=10 ng/ml) induced the release of HMG1 from human PBMCs in a time- and dose-dependent manner (Table 1). IFN-γ alone (0-200 U/ml) did not induce HMG1 release from any of the above cells, but when added in combination either with TNF or IL-1β, IFN-γ dose-dependently enhanced HMG1 release from macrophages, with a maximal 3-fold enhancement by IFN-γ at a concentration of 100 U/ml. The release of HMG1 was not due to cell death, because cell viability was unaffected by TNF, IL-1β, or LPS, as judged by trypan blue exclusion (90-92±5% viable for control vs. 88-95±4% in the presence of 100 ng/ml TNF, IL-1β or LPS). The amount of HMG1 released by pituicytes and macrophages inversely correlated with the intracellular concentration of HMG1, as determined by Western blotting analysis, indicating that the released material is, in part, derived from pre-formed cell-associated HMG1 protein.

Figure 5:
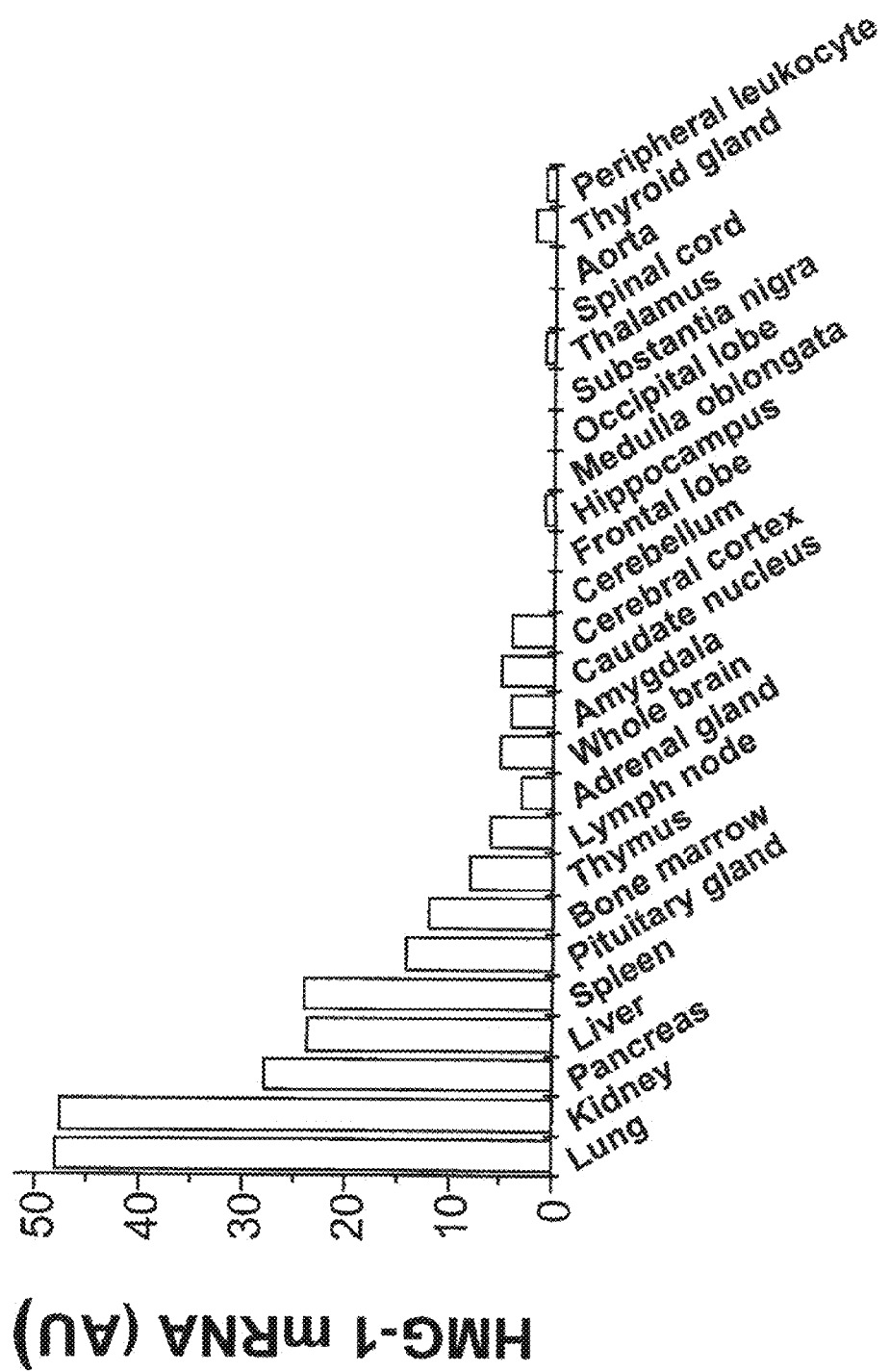
FIG. 5 shows the tissue distribution of HMG1 mRNA. Human RNA master blots containing poly(A)$^+$ RNA of various tissues (Clontech, Palo Alto, Calif., USA) were hybridized with a 0.6 kb digoxigenin-11-dUTP-labeled HMG1 cDNA probe synthesized by PCR using recombinant plasmid containing the HMG1 cDNA insert, all in accordance with methods well-known in the art. Briefly, hybridization was performed in a hybridization buffer (5×SSC/2% blocking reagent/0.1% SDS/50% formamide, Boehringer Mannheim, Indianapolis, Ind.) with a probe concentration of 10 ng/ml for 16 hours at 65° C. After hybridization, the filter was subject to two washes of 0.5×SSC/0.1% SDS for 5 minutes, and two washes of 0.2×SSC/0.1% SDS for 10 minutes at room temperature. Signal was detected using anti-digoxigenin antibodies conjugated to phosphotase and detection reagents 4-nitrobluetetrazolium chloride (NBT) and 5-cromo-4-chloro-3-indolyl-phosphate (BCIP) (Boehringer-Mannheim) according to standard methods. The blots were scanned with a silver image scanner (Silverscanner II, Lacie Limited, Beaverton, Oreg.), and relative optical density (in arbitrary units, AU) was quantified using NIH 1.59 image software. Note that highest levels were observed in macrophage-rich tissues.

Potential sources of circulating HMG1 in vivo were assessed by hybridization of an HMG1-specific probe to mRNA prepared from various normal human tissues (blot substrate available from commercial sources), with the results summarized in FIG. 5. Several macrophage-rich tissues (lung, liver, kidney, pancreas and spleen) exhibited the most abundant HMG1 mRNA expression; less was observed in pituitary, bone marrow, thymus, lymph node and adrenal gland. In addition to providing information as to the relative tissue distribution of HMG1 expression, this study shows the practicality and utility of assaying for HMG1-specific nucleic acid sequences in tissue samples.

Example 3

Recombinant HMG1 Administration, In Vitro and In Vivo

This example details procedures to produce HMG1 by well-known recombinant DNA technologies. The HMG1 open reading frame was amplified by PCR and subcloned into an expression vector (pCAL-n). Briefly, the 648-bp open reading frame of HMG1 cDNA was PCR amplified (94° C. 1', 56° C. 2', 72° C. 45", 30 cycles) from 5 ng Rat Brain Quick-Clone cDNA (Catalog #7150-1, Clontech, Palo Alto, Calif., USA) using primers containing the following sequences, 5'-CCC GCGGATCCA TCG AGG GAA GGA TGG GCA AAG GAG ATC CTA-3' [SEQ ID NO. 2], and 5'-CCC GC AAGCTTA TTC ATC ATC ATC ATC TTC T-3' [SEQ ID NO. 3]. The 680 bp PCR product (4 μg) was digested with Bam HI and Hind III, and cloned into the Bam HI/Hind III cloning sites of the pCAL-n vector (Stratagene, La Jolla, Calif., USA). The recombinant plasmid was transformed into E. coli BL21(DE3)pLyS (Novagen, Madison, Wis., USA), and positive clones were screened and confirmed by DNA sequencing on both strands using a Taq DyeDeoxy terminator cycle sequencing kit on the ABI 373A automated fluorescent sequences (Applied Biosystems, Foster City, Calif., USA).

To express recombinant HMG1, positive clones were cultured at 37° C. with vigorous shaking (250 rpm) until $OD_{600}$ reached 0.6, when IPTG (1 mM) was added. Twelve hours after IPTG induction, bacterial cells were harvested by centrifugation (6500 rpm, 15 minutes), and lysed by freeze-thaw cycles. The water-soluble fraction was collected after centrifugation (30 minutes, 12,000 rpm), and recombinant HMG1 was purified on a calmodulin-binding resin column as instructed by the manufacturer (Stratagene). Bacterial endotoxin was removed from the recombinant HMG1 by using Detoxi-Gel endotoxin-removing gel (Pierce, Rockford, Ill. USA, Cat. #20344), and residual LPS content was determined by the Limulus Amebocyte Lysate Test (LAL test, Cat. #50-648U, QCL-1000 Choromogenic LAL, Bio-Whittaker, Inc., Walkersville, Md., USA). Purified recombinant HMG1 was added to cultures of human peripheral blood mononuclear cells (HuPBMCs), and supernatants assayed for TNF by ELISA four hours after stimulation. The LPS-neutralizing agent polymyxin B (10 μg/ml) was added concurrently with recombinant HMG1 to eliminate the effect of any contaminating LPS on TNF release. Additionally, recombinantly derived HMG1 was administered to test animals, with or without the additional endotoxemic challenge of exogenous LPS, to study the pathogenic potential of high levels of HMG1 in vivo (see FIGS. 2B and 2C). In some experiments, serum samples were secured from HMG1-treated animals to be assayed for TNF as detailed herein (see FIG. 1B).

The above procedure provides recombinant HMG1 as a fusion peptide comprising a 3.0 kDa calmodulin-binding domain and a thrombin cleavage site as an amino terminal extension in register with the HMG1 peptide sequence. In some experiments, the fusion tag was removed from an aliquot of the recombinant protein and the bioactivity of the full fusion protein was compared to the cleaved HMG1 peptide; no significant difference in bioactivity was noted and additional experiments (especially those requiring administration of recombinantly produced HMG1 to animals) typically were conducted with the (uncleaved) fusion protein.

Figure 3A:
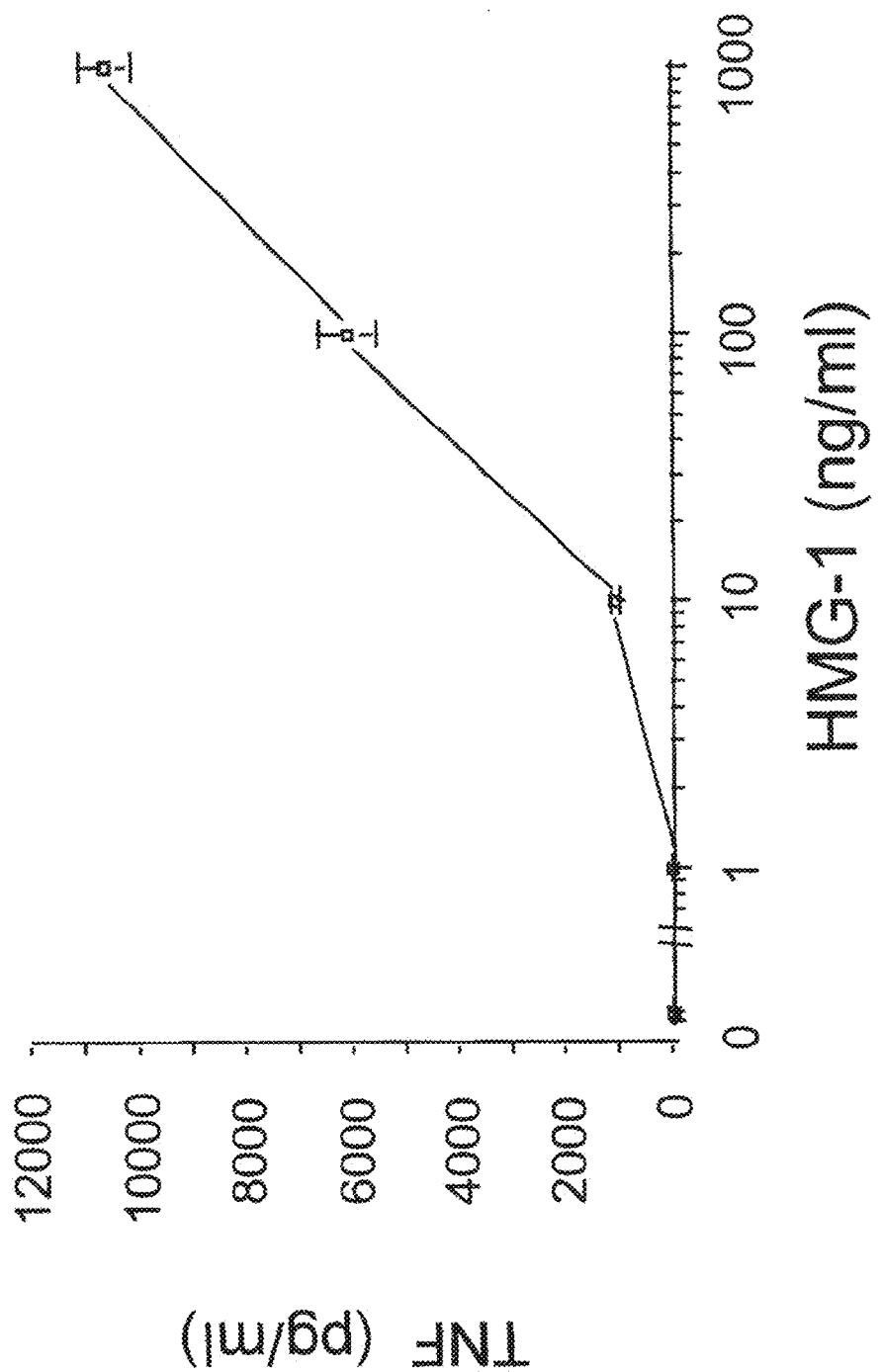
FIG. 3A shows that HMG1 induces TNF release from huPPBMCs in dose-dependent fashion. Freshly isolated huPBMC cultures were stimulated with purified recombinant HMG1 protein at the indicated doses, and culture media were sampled four hours later to be assayed for TNF according to known immunologic methods (ELISA).
Figure 3B:
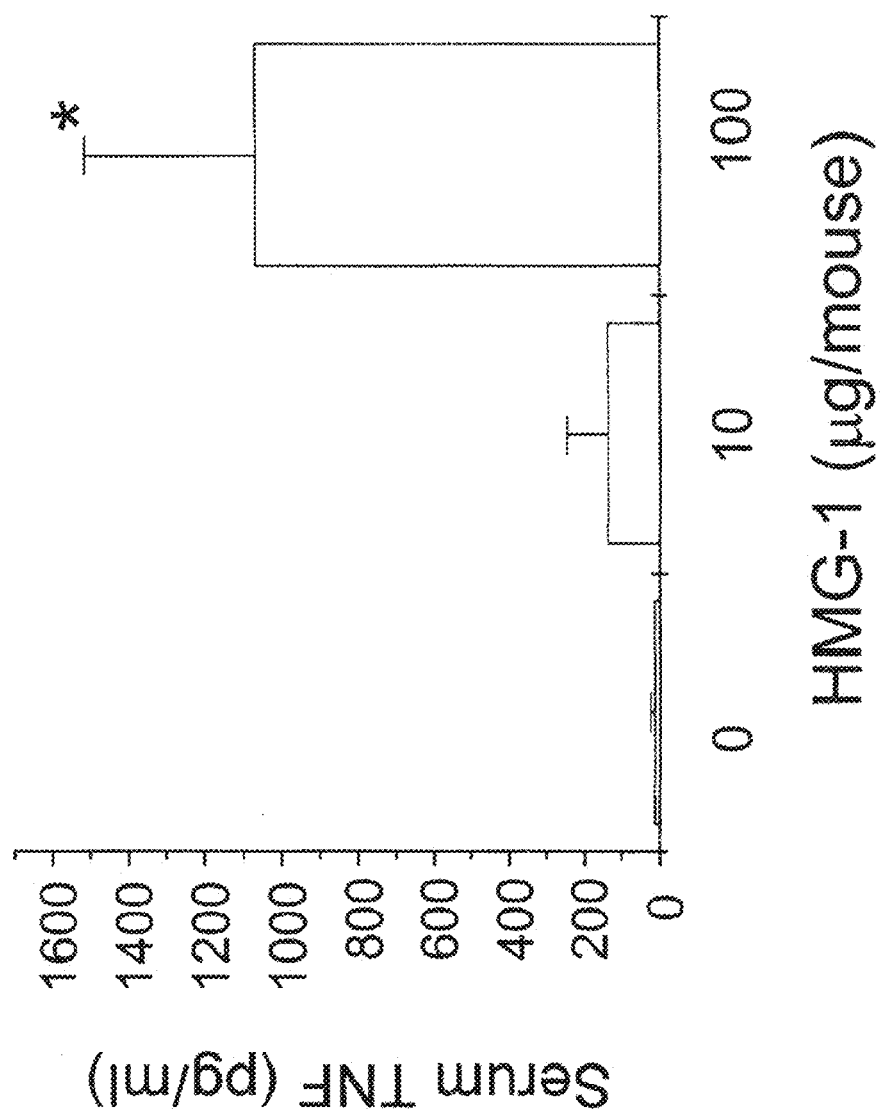
FIG. 3B shows that administration of HMG1 induced accumulation of TNF in serum of treated mice. Balb/C mice (20-23 g) were treated intraperitoneally with purified recombinant HMG1 at the indicated doses and blood samples were taken two hours later for assay of TNF by an L929 bioassay and (TNF levels expressed as mean±S.E.M., N=3).

As demonstrated in FIGS. 3A and 3B, in vitro or in vivo administration of recombinantly derived HMG1 induced a brisk TNF response, confirming the identification of HMG1 as a late-appearing LPS-induced macrophage-derived endogenous mediator with pro-inflammatory activity.

Example 4

Anti-HMG1 Antibodies and Immunodetection

This example provides the results of experiments to generate and use polyclonal antibodies against HMG1. Briefly, polyclonal antibodies against an oligopeptide corresponding to the N-terminal amino acid sequence of HMG1, or against purified recombinant HMG1, were generated in rabbits according to standard procedures well known in the art. Briefly, eight copies of an oligopeptide with the sequence GKGDPKKPRGKMSSC [SEQ ID NO. 4] were anchored to radially branching lysine dendrites (small immunogenically inert core). These large macromolecules were injected three times both subcutaneously and intradermally (0.5-1.0 mg per injection) into rabbits at week 1, 2, and 4 after pre-bleed at Day 0. Two weeks after the last immunization, rabbits were bled and boosted intramuscularly with 1.0 mg of antigen, followed by a second bleeding two weeks later. Alternatively, to produce polyclonal antibodies against recombinant HMG1, rabbits were immunized with recombinant HMG1 fusion peptide (100 μg per injection) following a similar protocol. Monoclonal antibodies reactive against HMG1 (i.e., that bind, and in some cases, neutralize or antagonize the biological activity of HMG1) are conveniently prepared according to methods well known in the art using the HMG1 antigens described herein or other HMG1 peptide fragments as immunogens. Such monoclonal antibodies, and/or the hybridomas that produce them, are useful to produce various "humanized" antibodies reactive against HMG1 (all according to methods known in the art), which humanized antibodies are useful as taught herein.

HMG1-specific antibodies were used to measure by Western blotting analysis the inducible release of HMG1 from RAW 264.7 cells after treatment with TNF or LPS (FIG. 1). Briefly, proteins were fractionated by SDS-PAGE on a 4-20% gradient gel, transferred to a PVDF membrane, and blotted with rabbit antiserum raised against either the N-terminal synthetic HMG1 antigen or against recombinant HMG1. The signal was detected using a ECL kit as instructed by the manufacturer (Amersham Life Science Inc., Arlington Heights, Ill., USA), and levels of HMG1 were determined by measuring optical intensity of bands on Western blots digitized for analysis using NIH 1.59 image software, with reference to a standard curve of purified recombinant HMG1.

Figure 1B:
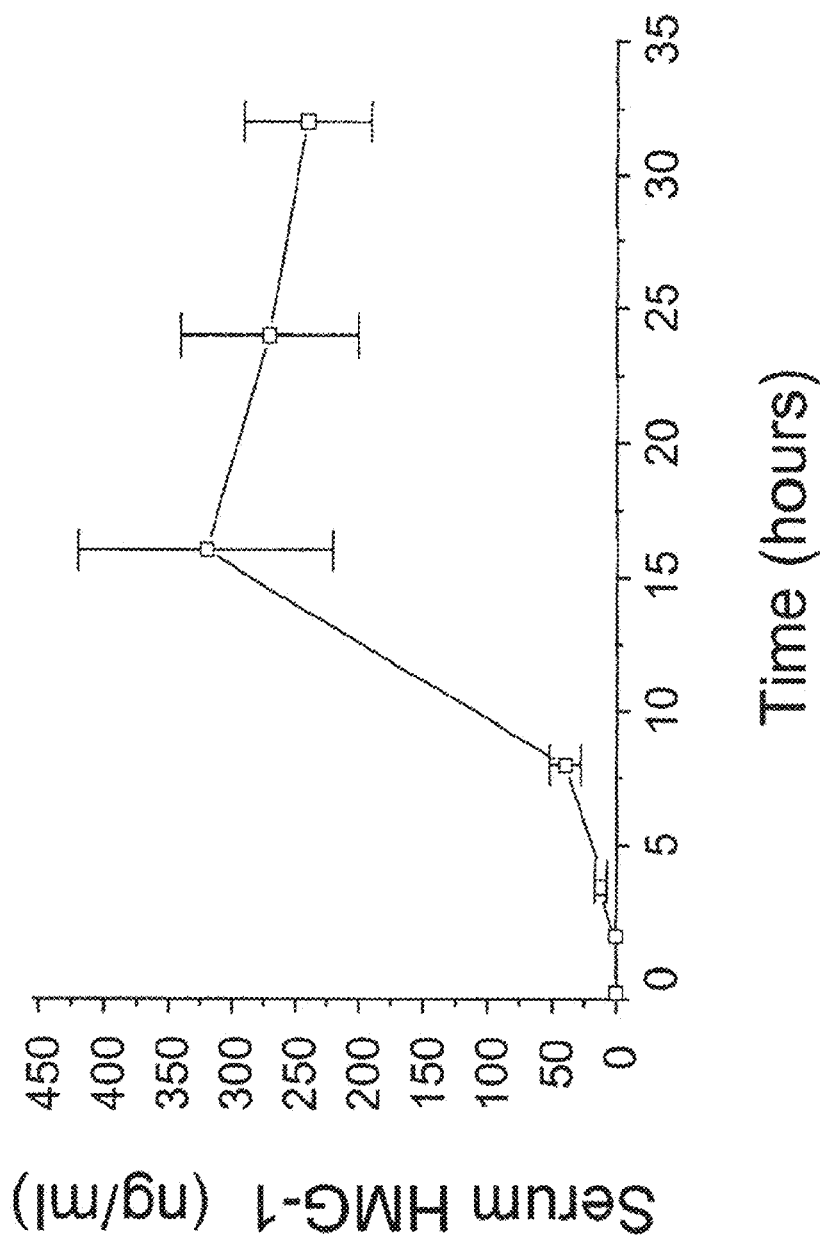
FIG. 1B shows accumulation of HMG1 in serum of LPS-treated mice. Serum from Balb/C mice was collected at various time points after LPS administration, and assayed for HMG1 by Western blotting using antibodies raised against recombinant HMG1.

No HMG1 protein was detected in RAW 264.7 cells-conditioned medium in the absence of TNF or LPS treatment, but HMG1 accumulated in conditioned medium to high levels after such stimulation, reaching a plateau at 8-28 hours after stimulation (FIG. 1A). In summary, the data presented in Examples 1, 3 and in FIG. 1A show that the release of HMG1 from macrophages is stimulus-specific and time- and dose-dependent, with maximal accumulation observed within 8 hours after stimulation with TNF at concentrations as low as 5 ng/ml. It is well appreciated that sepsis, septic shock and related conditions may occur in humans in response to stimuli that differ qualitatively or quantitatively from the single large, lethal LPS bolus used in this predictive model. Nevertheless, experimental endotoxemia has been a valuable and predictive model system by which to identify critical components of the inflammatory cytokine cascade and by which to identify specific antagonists with predicted clinical utility. In the regard, HMG1 antagonists are perhaps more therapeutically attractive than TNF antagonists in view of the later appearance of HMG1 versus TNF in the response to endotoxin.

Example 5

Detection of HMG in In Vivo Animal Models

This example illustrates an in vivo experiment in rodents measuring serum HMG1 levels after administration of a sub-lethal dose of LPS ($LD_{50}$). Mice or rats were treated with LPS, and sera were collected at different time points, and assayed for levels of HMG1 by Western blotting analysis. The serum concentrations of HMG1 were estimated by measuring the optical band intensity with reference to a standard curve of purified HMG1. Serum levels increased significantly by 16 hours after LPS, and remained high for at least 32 hours (FIG. 1B), and were not detectable in vehicle-treated control animals. These data show that HMG1 represents a particularly attractive target for diagnosis of, and pharmaceutical intervention against, sepsis and related disorders of cytokine toxicity because HMG1 is a late-appearing mediator in the inflammatory cytokine cascade.

Example 6

Benefits of Protection Against HMG1

This example provides the results of a predictive in vivo assay to measure therapeutic activity of antagonists of HMG1 in relation to treatment of sepsis and related conditions of cytokine-mediated toxicity. In this example, the HMG1 antagonist was an anti-HMG1 antibody preparation. Controls treated with pre-immune serum developed lethargy, piloerection, diarrhea, and succumbed to death within 48 hours. These clinical signs of endotoxemia were significantly prevented by administration of anti-HMG1 antibodies. Male Balb/C mice (6-7 weeks, 20-23 grams) were randomly grouped (10 animals per group) and pre-treated either with control (pre-immune) or anti-HMG1 serum (as made in Example 4) 30 minutes before administration (intraperitoneally) of a lethal dose of LPS (50 mg/kg in 1×PBS). Other experimental groups received additional doses of anti-HMG1 serum at +12 or, +12, and +36 hours after LPS administration. Animals were observed for appearance and survival for at least two weeks.

Polyclonal antibodies against recombinant HMG1 were generated in rabbits, and antiserum was assayed for specificity and titer by ELISA and Western blotting procedures. The polyclonal antiserum immunospecifically recognized (bound to) recombinant HMG1 in Western blot analysis, for instance, and discriminated rHMG1 from other proteins in both crude bacterial lysates and as a purified protein that had been diluted into mouse serum. Using chemiluminescence-amplified detection methods in Western blotting analysis, polyclonal anti-HMG1 antiserum at dilutions up to 1:1000 was useful to detect as little as 50 pg rHMG1 protein. Administration of anti-HMG1 antiserum in the indicated (FIG. 2A) amounts at −0.5 (if one dose), −0.5 and 12 (if two doses), or −0.5, 12 and 36 (if three doses) hours relative to LPS challenge (at time 0) was protective against LPS-induced lethality, and repeated dosing schedules provided better protection.

Figure 2A:
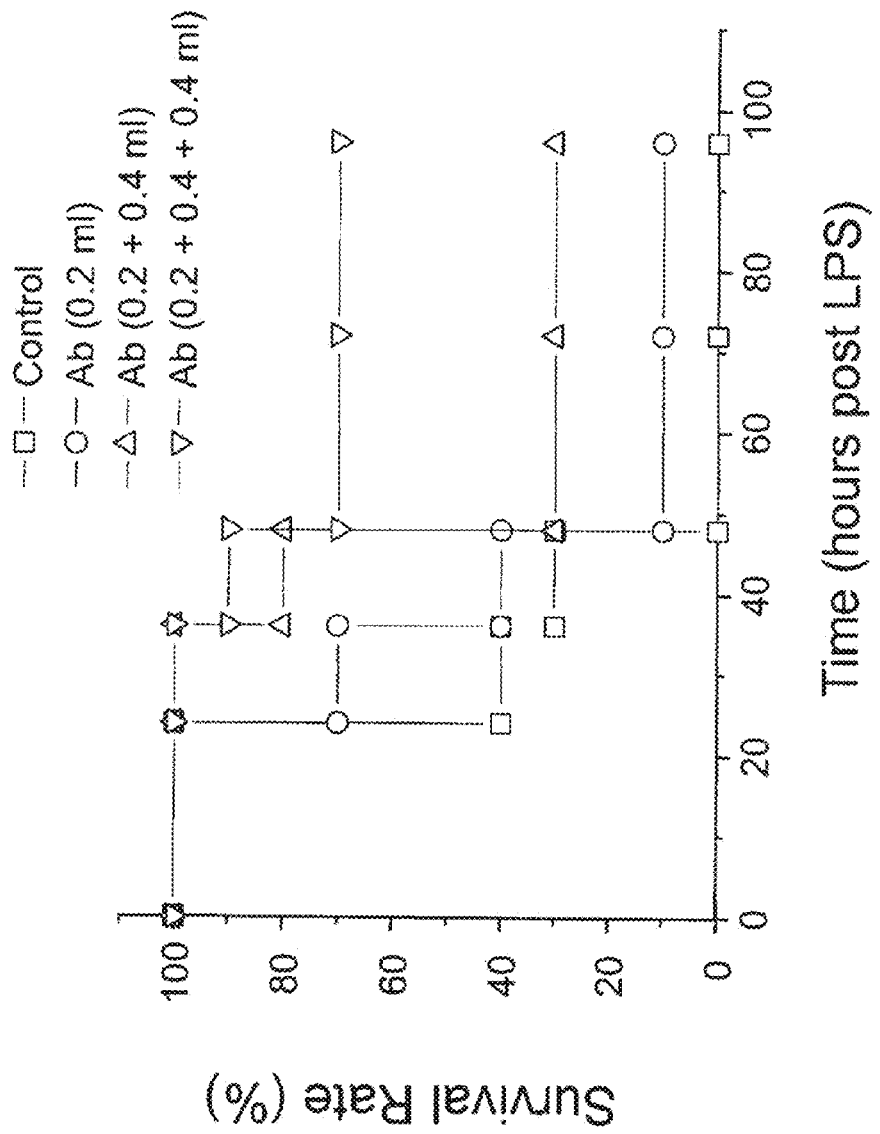
FIG. 2A shows the protective effect of anti-HMG1 antibodies against LPS lethality, tested in mice. Administration of anti-HMG1 antiserum in the indicated amounts at −0.5 (if one dose), −0.5 and 12 (if two doses), or −0.5, 12 and 36 (if three doses) hours relative to LPS challenge (at time 0) was protective against LPS-induced lethality, and repeated dosing schedules provided better protection.
Figure 2B:
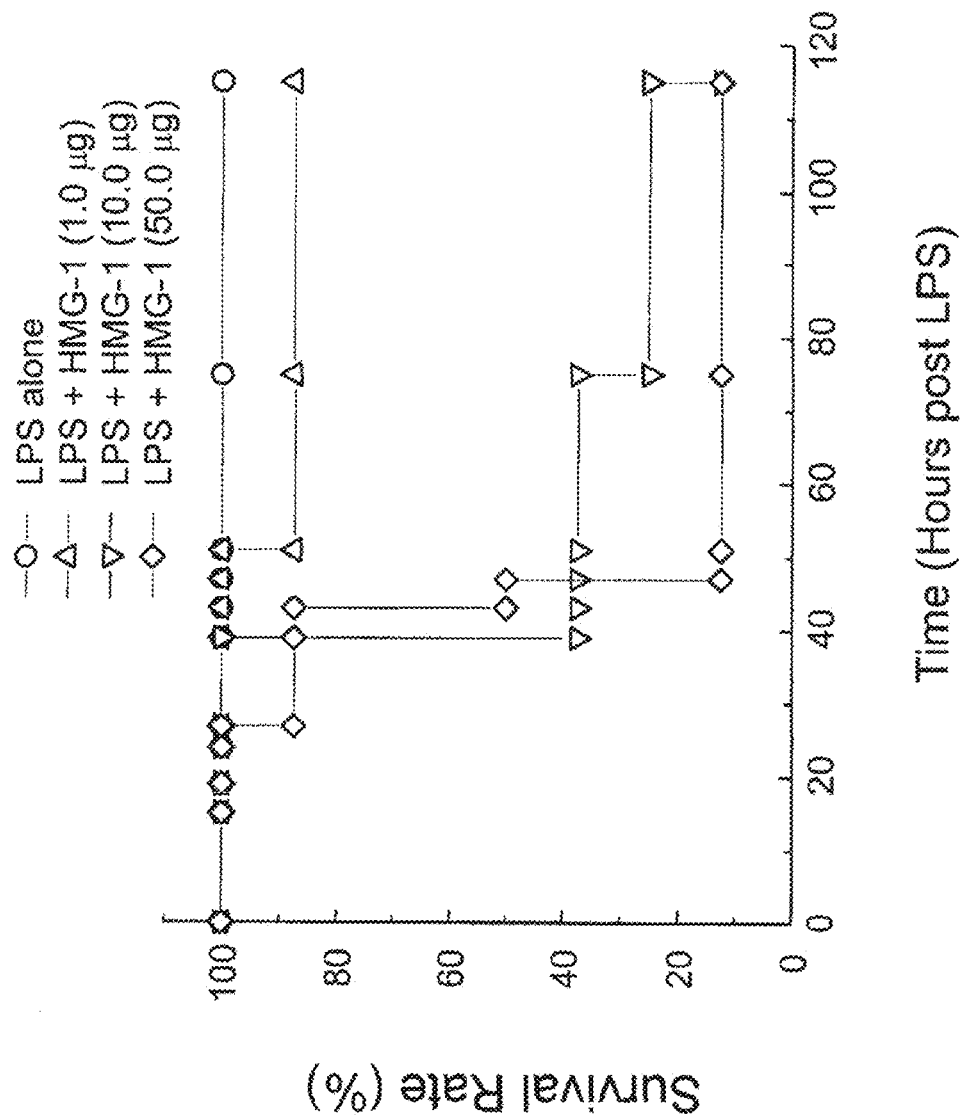
FIG. 2B illustrates that rHMG1 caused dose-dependent lethality in endotoxic mice. Male Balb/C mice (20-23 grams) were randomized in groups of ten to receive LPS (3.15 mg/kg; a non-lethal dose) alone or in combination with purified recombination HMG1 protein. Administration of HMG1 at the indicated doses 2, 16, 28 and 40 hours after LPS challenge significantly increased the lethality of the underlying endotoxemia.

FIG. 2B illustrates that rHMG1 causes dose-dependent lethality in endotoxic mice. Male Balb/C mice (20-23 grams) were randomized in groups of ten to receive LPS (3.15 mg/kg; a non-lethal dose) alone or in combination with purified recombinant HMG1 protein. Administration of HMG1 at the indicated doses 2, 16, 28 and 40 hours after LPS challenge significantly increased the lethality of the underlying endotoxemia.

Figure 2C:
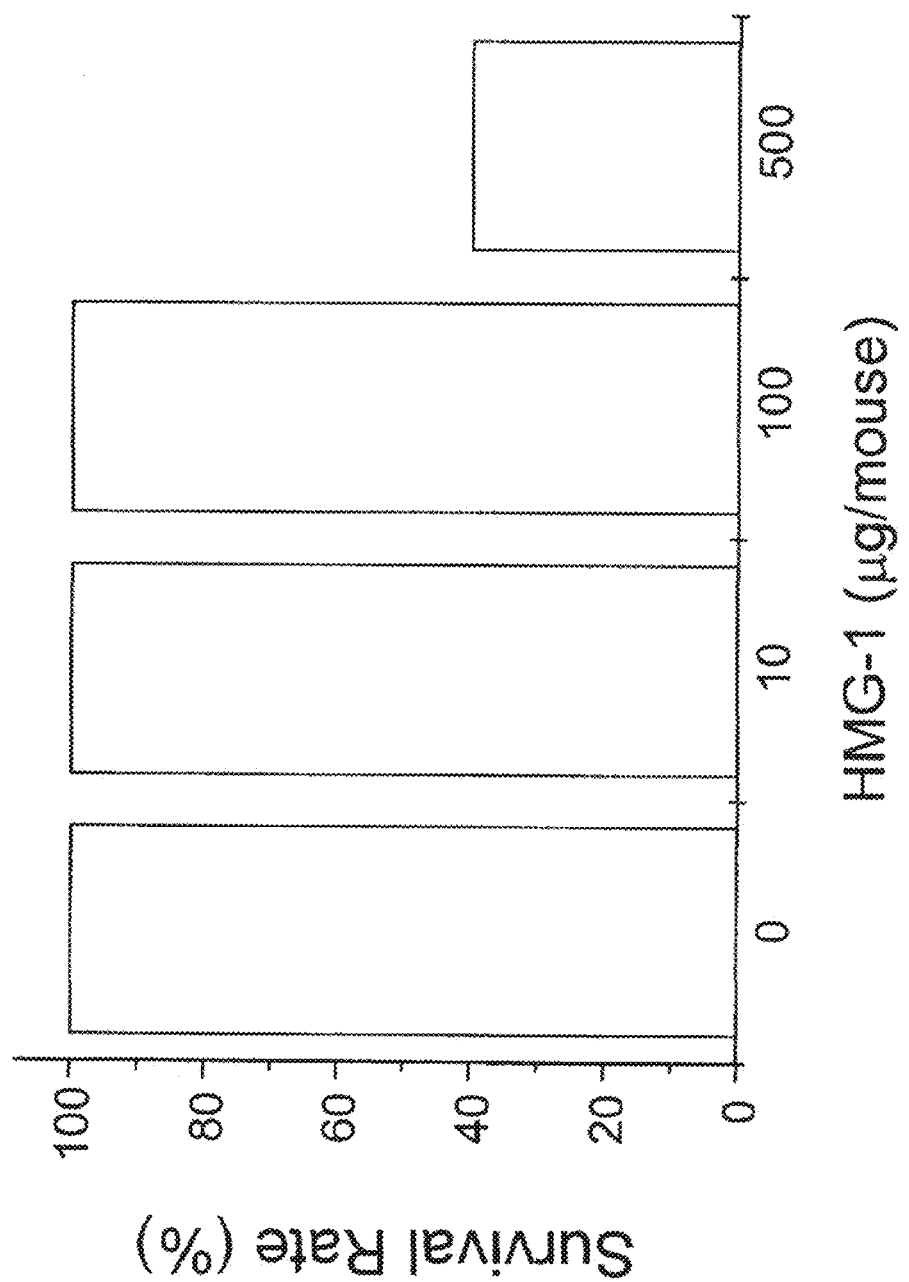
FIG. 2C illustrates independent lethal toxicity of HMG1 as a function of dose. Purified rHMG1 was administered to male Balb/C mice (five mice per treatment group) as a single i.p. bolus at the indicated dosage. Mice were observed for at least 48 hours, and 60% of mice treated with rHMG1 at a dose of 500 μg/mouse died within 24 hours of rHMG1 challenge, indicating a single dose $LD_{50}$ of less than 500 μg/mouse.

FIG. 2C illustrates the independent lethal toxicity of HMG1 as a function of dose. Purified rHMG1 was administered to male Balb/C mice (five mice per treatment group) as a single i.p. bolus at the indicated dosage. Mice were observed for at least 48 hours, and 60% of mice treated with rHMG1 at a dose of 500 μg/mouse died within 24 hours of rHMG1 challenge, indicating a single dose $LD_{50}$ of less than 500 μg/mouse.

The protection conferred by anti-HMG1 antibodies was specific, because administration of pre-immune serum, which showed no immunospecific reactivity to HMG1 on Western blots, did not spare subjects from LPS-mediated mortality (FIG. 2A). Moreover, HMG1-specific antibodies did not cross-react with other macrophage-derived cytokines (e.g. IL-1 and TNF), eliminating the possibility that antibodies conferred protection by binding and thereby neutralizing these mediators. Protection against sepsis, sepsis associated pathogenesis and sepsis-related diseases involving activation of pro-inflammatory cytokine cascades may be improved by combination therapy targeted against more than one component of the cytokine cascade. Antagonists of HMG1 in this regard can be combined with specific antagonists of TNF, IL-1, MIF and other inflammatory mediators, or with more broadly active antagonists of inflammatory responses that inhibit multiple components of the inflammatory cascade (e.g., aspirin, NSAIDS, anti-inflammatory steroids, etc.), to provide even more effective therapeutic modalities. Protection against LPS toxicity was antibody dose-related, and more frequent dosing with higher amounts of antibody reduced mortality by up to 70% (FIG. 2A). Mice were observed for at least 2 weeks in all experiments, and no late mortality occurred, indicating that anti-HMG1 antibody treatment confers lasting protection against LPS lethality, and does not merely delay the time of death.

Example 7

HMG1 in Human Disease

This example provides data that establish an association between HMG1 and human sepsis, and thereby support an indication for using HMG1 antagonists generally and anti-HMG1 antibodies in particular in human sepsis and related conditions of cytokine toxicity. Serum HMG1 levels in normal healthy individuals and critically ill patients were measured using the polyclonal antibodies generated as in Example 4 in a Western blot format with reference to a standard curve of rHMG1. HMG1 was not detectable in normal controls, but accumulated to high levels in critically ill patients with sepsis (Table 2).

TABLE 2

Serum appearance of HMG1 in sepsis patients.

| Patient (#) | Age (year) | HMG1 (ng/ml) | Diagnosis | Outcome |
| --- | --- | --- | --- | --- |
| 1 | 27 | <d.l. | Normal | Healthy |
| 2 | 34 | <d.l. | Normal | Healthy |
| 3 | 35 | <d.l. | Normal | Healthy |
| 4 | 36 | <d.l. | Normal | Healthy |
| 5 | 61 | <d.l. | Normal | Healthy |
| 6 | 31 | <d.l. | Normal | Healthy |
| 7 | 55 | 10 | Sepsis, anastomotic leak | Recovered |
| 8 | 70 | 7-20 | Sepsis, colonic perforation | Recovered |
| 9 | 44 | 10-60 | Sepsis, MOF, spinal reconstruction | Died |
| 10 | 60 | >120 | Sepsis, MOF, perforated gastric ulcer | Died |
| 11 | 47 | >120 | Sepsis, MOF, pneumonia | Died |

Note:
<d.l.—below detection limit;
MOF—Multiple Organ Failure.

These data show that elevated serum HMG1 levels are observed in patients with sepsis, and the highest levels of serum HMG1 are observed in lethal cases (Table 2). These data further indicate the therapeutic importance of HMG1 antagonists in sepsis and also provide evidence for the diagnostic utility of an assay for sepsis and severity (i.e., potential lethality) of sepsis by measuring serum concentrations of HMG1. This diagnostic assay is also useful for diagnosing the severity of allied conditions involving activation of the inflammatory cytokine cascade.

Figure 6:
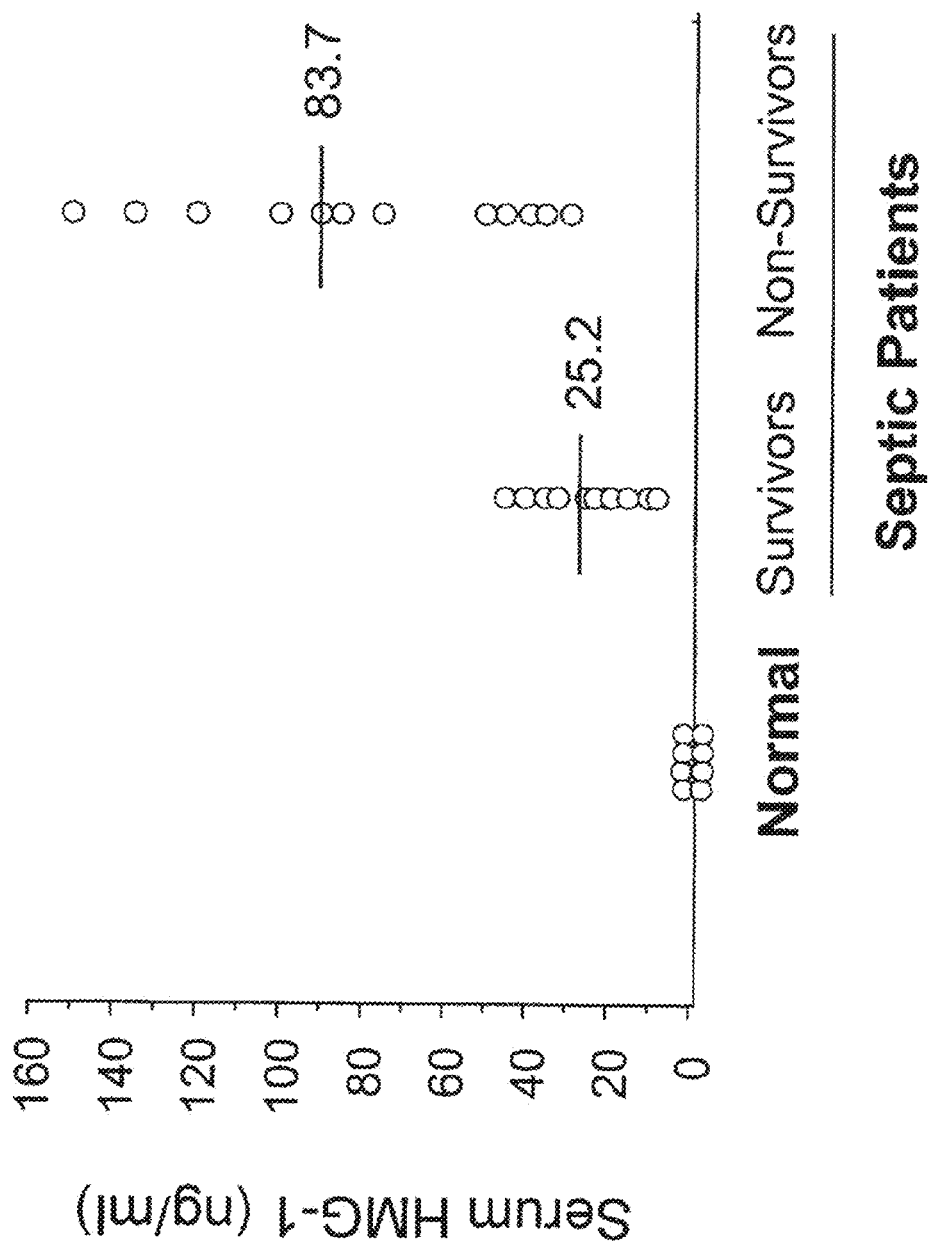
FIG. 6 shows, in comparison to a group of normal control subjects, increased human serum HMG1 levels as detected in hospitalized human subjects with sepsis, wherein the septic patients have been further categorized as to whether the patient died or survived.

Additional subjects were screened for serum HMG1 levels in association with lethal versus non-lethal sepsis, with results (cumulative with Table 2) as described in FIG. 6. The data summarized in FIG. 6 represent serum samples obtained from eight healthy subjects and twenty-five septic patients infected with Gram positive [*Bacillus fragilis* (1 patient), *Enterococcus facecalis* (1 patient), *Streptococcus pneumonia* (4 patients), *Listeria monocytogenes* (1 patient), or *Staphylococcus aureus* (2 patients)], Gram negative [*Escherichia coli* (7 patients), *Klebsiella pneumonia* (1 patient), *Acinetobacter calcoaceticus* (1 patient), *Pseudomonas aeruginosa* (1 patient), *Fusobacterium nucleatum* (1 patient), *Citrobacter freundii* (1 patient)], or unidentified pathogens (5 patients). Serum was fractioned by SDS-PAGE gel electrophoresis, and HMG1 levels were determined by Western blotting analysis with reference to standard curves of purified rHMG1 diluted in normal human serum. The detection limit by Western blotting analysis is 50 pg. Note that HMG1 is not detectable in normal controls, but significantly increased in septic patients. The average level of HMG1 in serum of non-surviving septic patients (N=13 patients, mean HMG1 level=83.7±22.3 ng/ml) is significantly higher than in survivors (N=12, mean HMG1 level=25.2±15.1 ng/ml, $P<0.05$). These data provide direct evidence of the utility of screening tissue (including, without limitation blood or serum) samples for HMG1 sequences (protein or nucleic acid) as a diagnostic and prognostic indicator of the presence of sepsis and related disorders of cytokine activation and of the severity and likely clinical course of such diseases and conditions.

Example 8

HMG1 Induces Pro-Inflammatory Mediators and Weight Loss

The present results provide evidence that HMG1 is a late released mediator element of the inflammatory cytokine cascade. Addition of recombinant HMG1 to primary human peripheral blood mononuclear cells led to the dose-dependent induction of TNF within four hours after stimulation (FIG. 3A). This stimulation by recombinant HMG1 of TNF release by HuPBMCs was not due to LPS contamination because: i) purified recombinant HMG1 was not contaminated by LPS as judged by an LAL endotoxin assay; ii) addition of the LPS-neutralizing agent polymyxin B did not affect HMG1-induced TNF release; and iii) proteolytic cleavage of recombinant HMG1 preparations with trypsin completely abolished the TNF release activity for the PBMC cultures. HMG1 stimulation also induced macrophages to release nitric oxide (NO).

To confirm that HMG1 induced serum TNF release in vivo, purified recombinant HMG1 was administered intraperitoneally to Balb/C mice, and blood samples were collected to be assayed for TNF by the L929 assay. As shown in FIG. 3B, TNF was not detectable in serum of control animals, but was significantly increased two hours after administration of recombinant HMG1 protein.

Figure 4:
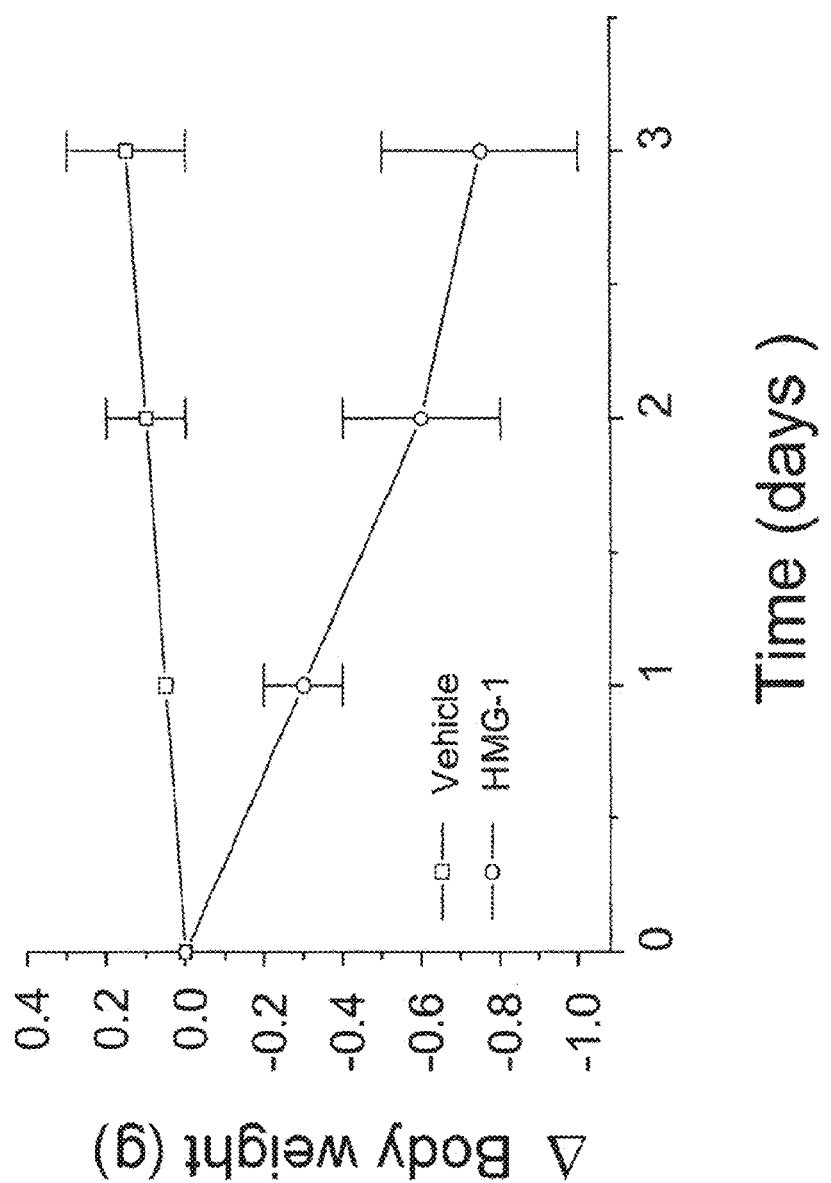
FIG. 4 shows that HMG1 caused body weight loss in mice. Purified HMG1 was administered intraperitoneally to mice at 100 μg/mouse/day for three days, and body weight was monitored.

Repetitive administration of recombinant gene product of the HMG1 gene (100 µg/mouse/day) caused significant body weight loss (FIG. 4) in mice. Without limitation as to mechanism and without being bound by theory, these data are consistent with the hypothesis that HMG1 acts as a feed-forward stimulator of the pro-inflammatory cascade under both in vitro and in vivo conditions. These in vivo data in a predictive model of weight loss also provide predictive evidence that a pharmaceutical formulation comprising HMG1, or a therapeutically active fragment thereof, is an effective weight loss therapy.

Example 9

In Vivo Sources of HMG1

Serum HMG1 levels in hypophysectomized versus control rats also were measured by quantitation of Western blot intensities as described above. There were significantly higher HMG1 levels within 12 hours after endotoxic challenge (LPS at 1.0 mg/kg) in hypophysectomized rats (approx. 75 ng/ml) as compared to controls (approx. 25 ng/ml). These results indicate that pituicytes are not the major source of serum HMG1 levels and that macrophages may play a quantitatively more important role.

What is claimed is:

1. A pharmaceutical composition comprising an effective amount of an antagonist of high mobility group 1 (HMG1) protein, wherein the amount of the antagonist is effective to inhibit HMG1-mediated activation of the inflammatory cytokine cascade, and wherein the HMG1 antagonist is selected from an antibody that specifically binds to HMG1, an antigen-binding fragment of said antibody, or an HMG1 antisense sequence, wherein the HMG1 comprises an antigenic fragment of SEQ ID NO: 4.

2. The composition of claim 1, which is in the form of a tablet, pill, capsule, liquid, gel, syrup, slurry, suspension, skin

---

SEQUENCE LISTING

```
<160> NUMBER OF SEQ ID NOS: 5

<210> SEQ ID NO 1
<211> LENGTH: 14
<212> TYPE: PRT
<213> ORGANISM: Homo sapiens

<400> SEQUENCE: 1

Gly Lys Gly Asp Pro Lys Lys Pro Arg Gly Lys Met Ser Ser
 1               5                  10

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2
cccgcggatc catcgaggga aggatgggca aaggagatcc ta                         42

<210> SEQ ID NO 3
<211> LENGTH: 31
<212> TYPE: DNA
<213> ORGANISM: Artificial Sequence
<220> FEATURE:
<223> OTHER INFORMATION: primer

<400> SEQUENCE: 3
cccgcaagct tattcatcat catcatcttc t                                     31

<210> SEQ ID NO 4
<211> LENGTH: 15
<212> TYPE: PRT
<213> ORGANISM: Artificial Sequence
<220> FEATURE:
<223> OTHER INFORMATION: antigen

<400> SEQUENCE: 4

Gly Lys Gly Asp Pro Lys Lys Pro Arg Gly Lys Met Ser Ser Cys
 1               5                  10                  15

<210> SEQ ID NO 5
<211> LENGTH: 42
<212> TYPE: DNA
<213> ORGANISM: Artificial Sequence
<220> FEATURE:
<223> OTHER INFORMATION: antisense oligonucleotide

<400> SEQUENCE: 5
gaggaaaaat aactaaacat gggcaaagga gatcctaaga ag                         42
``` patch, topical cream, mucosal patch, mucosal liquid, mucosal gel, or is suitable for administration to the respiratory tract by inhaler.

3. The composition of claim 1, further comprising a solid excipient selected from a sugar, a cellulose preparation, a gelatin, a gum, polyvinylpyrrolidone, or a combination thereof.

4. The composition of claim 1, further comprising a disintegrating agent and/or stabilizer.

5. A method of treating a TNF-mediated, IL-1-mediated, or lipopolysaccharide (LPS)-mediated activation of the inflammatory cytokine cascade, comprising administering an effective amount of the composition of claim 1.

6. The method of claim 5, wherein the HMG1 antagonist is an antibody or antigen-binding fragment thereof that inhibits HMG-1-mediated activation of the inflammatory cytokine cascade.

\* \* \* \* \*